US012295782B2

(12) United States Patent
Cermak et al.

(10) Patent No.: US 12,295,782 B2
(45) Date of Patent: May 13, 2025

(54) PARALLEL PATH PUNCTURE DEVICE GUIDE AND METHOD

(71) Applicant: INNOVACELL GMBH, Innsbruck (AT)

(72) Inventors: Craig Joseph Cermak, Iowa City, IA (US); Rainer Marksteiner, Schwaz (AT); Marco Thurner, Innsbruck (AT)

(73) Assignee: INNOVACELL GMBH, Innsbruck (AT)

( * ) Notice: Subject to any disclaimer, the term of this patent is extended or adjusted under 35 U.S.C. 154(b) by 0 days.

(21) Appl. No.: 18/001,926

(22) PCT Filed: Jun. 15, 2021

(86) PCT No.: PCT/EP2021/066086
§ 371 (c)(1),
(2) Date: Dec. 15, 2022

(87) PCT Pub. No.: WO2021/255016
PCT Pub. Date: Dec. 23, 2021

(65) Prior Publication Data
US 2023/0240643 A1    Aug. 3, 2023

Related U.S. Application Data

(60) Provisional application No. 63/039,515, filed on Jun. 16, 2020.

(51) Int. Cl.
*A61B 8/08* (2006.01)
*A61B 8/00* (2006.01)

(52) U.S. Cl.
CPC ............ *A61B 8/085* (2013.01); *A61B 8/4218* (2013.01)

(58) Field of Classification Search
CPC ........ A61B 17/3403; A61B 2017/3413; A61B 2017/3405
See application file for complete search history.

(56) References Cited

U.S. PATENT DOCUMENTS 4,776,346 A    10/1988  Behara et al.
4,869,258 A     9/1989  Hetz
(Continued)

FOREIGN PATENT DOCUMENTS

CN    105380677 A     3/2016
CN    107261263 A    10/2017
(Continued)

OTHER PUBLICATIONS

Frudinger, A. et al. "Skeletal muscle-derived cell implantation for the treatment of sphincter-related faecal incontinence," *Stem Cell Research & Therapy*, 9.233 (2018): 1-20.
(Continued)

*Primary Examiner* — Joel Lamprecht
*Assistant Examiner* — Nyrobi Celestine
(74) *Attorney, Agent, or Firm* — Parker Highlander PLLC

(57) ABSTRACT

A guidance device is provided for facilitating the placement of a puncture device (a needle) at a defined position relative to an ultrasound probe. The guidance device provides additional support of a needle tip near the needle injection site to maintain a selected path throughout an injection. The additional support is automatically retracted for simple disposal with the used syringe after an injection. The guidance device minimizes contact of soiled components and enables syringe insertion, alignment, and removal for multiple different injections without removal of an ultrasound probe from the patient. More particularly, this invention relates to a puncture device guide, comprising: an adapter configured to fixedly attach to an ultrasound probe; a syringe holder
(Continued)

assembly configured to slidingly attach to the adapter and receive a syringe therein; wherein the syringe holder assembly is configured to slide on probe adapter in an axial direction relative to the ultrasound probe; wherein the syringe holder assembly is configured to allow for selective adjustment of a radial distance for a path of a needle of the syringe relative to the ultrasound probe; wherein the adapter includes a tip guide to selectively align a distal end of the needle with the radial distance for the path; and wherein, when the ultrasound probe is inserted into a patient, the syringe assembly is configured to slide forward on the adapter to insert the needle past the tip guide into a patient. The present invention further relates to a method of performing an injection, in particular by using a puncture device guide according to the present invention and to a guide plate configured to be used with a puncture device guide according to the present invention.

19 Claims, 10 Drawing Sheets

(56) References Cited

U.S. PATENT DOCUMENTS

| | | | |
|---|---|---|---|
| 4,877,033 | A | 10/1989 | Seitz, Jr. |
| 4,883,059 | A | 11/1989 | Stedman et al. |
| 4,892,520 | A | 1/1990 | Gilbaugh |
| 4,899,756 | A | 2/1990 | Sonek |
| 4,900,303 | A | 2/1990 | Lemelson |
| 5,078,144 | A | 1/1992 | Sekino et al. |
| 5,235,987 | A | 8/1993 | Wolfe |
| 5,494,039 | A | 2/1996 | Onik et al. |
| 6,309,374 | B1 | 10/2001 | Hecker et al. |
| 8,926,494 | B1 | 1/2015 | Cook et al. |
| 2002/0156376 | A1 | 10/2002 | Wang et al. |
| 2005/0059891 | A1 | 3/2005 | Kosaku |
| 2006/0020211 | A1 | 1/2006 | Tokumoto et al. |
| 2011/0098735 | A1 | 4/2011 | Lamps et al. |
| 2012/0245455 | A1 | 9/2012 | Bauman et al. |
| 2012/0259221 | A1 | 10/2012 | Sheldon |
| 2014/0200445 | A1 | 7/2014 | Boezaart et al. |
| 2014/0290666 | A1 | 10/2014 | Agee et al. |
| 2015/0250447 | A1* | 9/2015 | Kubota ............. A61B 17/3403 600/464 |
| 2016/0022309 | A1 | 1/2016 | Allaway |
| 2016/0128719 | A1 | 5/2016 | Cermak |
| 2017/0020558 | A1 | 1/2017 | Xu et al. |
| 2017/0340308 | A1* | 11/2017 | Cermak ................. A61B 8/12 |
| 2019/0223977 | A1 | 7/2019 | Galili et al. |
| 2019/0282262 | A1 | 9/2019 | Bouazza-Marouf et al. |
| 2020/0100778 | A1 | 4/2020 | Fisher et al. |
| 2020/0214739 | A1 | 7/2020 | Shi |
| 2021/0338267 | A1 | 11/2021 | Allaway |
| 2022/0096065 | A1 | 3/2022 | Fisher et al. |
| 2022/0168012 | A1* | 6/2022 | Wen .................... A61B 8/4483 |
| 2022/0378466 | A1 | 12/2022 | Cermak |

FOREIGN PATENT DOCUMENTS

| | | |
|---|---|---|
| CN | 109771811 A | 5/2019 |
| EP | 0 446 645 | 9/1991 |
| EP | 1 337 183 | 8/2003 |
| EP | 2 170 440 | 4/2010 |
| FR | 2 895 681 | 7/2007 |
| JP | 2008212608 A | 9/2008 |
| JP | 2020048690 A | 4/2020 |
| WO | WO 95/02663 | 1/1995 |
| WO | WO 2006/128718 | 12/2006 |
| WO | WO 2019/056784 A1 | 3/2019 |
| WO | WO 2021/067734 | 4/2021 |

OTHER PUBLICATIONS

International Search Report and Written Opinion issued in International Application No. PCT/US2020/053988, mailed Jan. 25, 2021.
International Search Report and Written Opinion issued in International Patent Application No. PCT/EP2021/066086, dated Oct. 5, 2021.
Messner, F. et al.,"Myogenic progenitor cell transplantation for muscle regeneration following hindlimb ischemia and reperfusion," *Stem Cell Research & Therapy*, 12.146 (2021): 1-15.
Thurner, M. et al., "Generation of myogenic progenitor cell-derived smooth muscle cells for sphincter regeneration," *Stem Cell Research & Therapy*, 11.233 (2020): 1-17.
Office Action issued in Chinese Patent Application No. 202080063058.4, dated Oct. 30, 2024. (with English translation).
Office Action issued in Japanese Patent Application No. 2022-574618, dated Jan. 21, 2025.

* cited by examiner

PARALLEL PATH PUNCTURE DEVICE GUIDE AND METHOD

CROSS-REFERENCE TO RELATED APPLICATIONS

This application is a national phase application under 35 U.S.C. § 371 of International Application No. PCT/EP2021/066086, filed Jun. 15, 2021, which claims benefit of priority to U.S. Provisional Application No. 63/039,515, filed Jun. 16, 2020. The entire contents of each of the aforementioned applications is hereby incorporated by reference.

FIELD OF THE INVENTION

This invention relates to puncture device guidance devices for use with medical imaging instruments and more particularly to devices for guiding puncture devices to repeatable locations on a patient relative to a medical imaging instrument probe. More particularly, this invention relates to a puncture device guide, comprising: an adapter configured to fixedly attach to an ultrasound probe; a syringe holder assembly configured to slidingly attach to the adapter and receive a syringe therein; wherein the syringe holder assembly is configured to slide on probe adapter in an axial direction relative to the ultrasound probe; wherein the syringe holder assembly is configured to allow for selective adjustment of a radial distance for a path of a needle of the syringe relative to the ultrasound probe; wherein the adapter includes a tip guide to selectively align a distal end of the needle with the radial distance for the path; and wherein, when the ultrasound probe is inserted into a patient, the syringe assembly is configured to slide forward on the adapter to insert the needle past the tip guide into a patient. The present invention further relates to a method of performing an injection, in particular by using a puncture device guide according to the present invention and to a guide plate configured to be used with a puncture device guide according to the present invention. Thus, a guidance device is provided for facilitating the placement of a puncture device (a needle) at a defined position relative to an ultrasound probe. The guidance device provides additional support of a needle tip near the needle injection site to maintain a selected path throughout an injection. The additional support is automatically retracted for simple disposal with the used syringe after an injection. The guidance device minimizes contact of soiled components and enables syringe insertion, alignment, and removal for multiple different injections without removal of an ultrasound probe from the patient.

BACKGROUND OF THE INVENTION

Imaging instruments, such as ultrasound probes, have revolutionized the manner in which many important medical procedures are performed. These medical instruments utilize imaging techniques to explore and assess the condition of human tissue and/or organs. As a result, diagnostic and therapeutic protocols have been developed that allow many highly successful and safe procedures to be performed with minimal disturbance to patients. For example, ultrasound probes have become an accepted modality for exploring endocavities, e.g., the digestive and reproductive tracts, of humans and animals in order to conduct routine examinations, as well as to identify evidence of tumors or other tissue regions of interest.

Puncture device guides are required to allow precise guiding of a puncture device when moving the puncture device within tissue of a subject. As puncture devices such as e.g. cannulas (hollow needles) used for penetration of tissue are mostly designed to have an asymmetric bevel and sharp edges, the incision and moving of the puncture device within tissue causes the puncture device to not only move in the axis it is pushed. Unequally arising frictional resistance along the bevel causes the needle to move also in other directions. Puncture device guides that also compensate such movement are required.

WO2021067734 discloses a device for use with an ultrasound probe and for guiding puncture devices. This device however has the disadvantage, that the tip of a puncture device (e.g. needle or cannula) is not sufficient stabilized to compensate the forces resulting from moving an asymmetrically beveled needle within a tissue, and thus can result in inaccurate movement of the puncture device within the subject. Further the device might accidentally be pushed into the endocavity of a patient thereby resulting in contamination of the device and possibly damage of the patient's tissue. If the device is contaminated e.g. by feces of the rectal endocavity and repeated guidance of a puncture device would cause the puncture device to touch the contaminated area, the risk of infecting the patient exists when the puncture device is penetrating the patient's tissues. Such risk could only be avoided by replacing and/or cleaning (e.g. sterilizing) the device in between repeated use for the same patient.

EP2170440A2 discloses an injection device for use with medical instruments and for guiding puncture devices. The device comprises a guiding tube wherein a puncture device is fitted to not freely move when penetrating and/or moving within tissue of a subject. However, when removing the puncture device from the puncture device guide, the puncture device needs to be pulled back through the guiding tube, thereby depositing tissue and contaminated material (e.g., feces) attached to the tip of the puncture device guide or puncture device within the guiding tube. Re-use of the device by pushing along the guide tube another puncture device would cause the deposited material to stick on the puncture device and being transported into the subject when penetrating the surface of the subject. This could cause infection and/or inflammation of the tissue in said subject and needs to be avoided. Further the device might accidentally be pushed into the endocavity of a patient thereby resulting in contamination of the device and possibly damaging patient's tissue. If the device is contaminated e.g. by feces of the rectal endocavity, repeated guidance of a puncture device would cause the puncture device to touch the contaminated area leading to increased risk of infecting the patient when the puncture device is penetrating the patient's tissues. Such risk could only be avoided by replacing and/or cleaning (e.g. sterilizing) the device in between repeated use for the same patient. Using the device of EP2170440A2 for repeated accurate injections thus can only be facilitated by cleaning the device or using a new device.

None of the above-mentioned disclosures, discloses a puncture device guide for accurate and safe repeatable guidance of a puncture device for injecting specific locations on and/or in a patient.

SUMMARY OF THE INVENTION

The present invention was made in light of the prior art described above. Thus, the object of the present invention is the provision of puncture device guide for use with medical imaging instruments and more particularly to devices for accurately and repeatably guiding puncture devices to locations on and/or in a patient relative to a medical imaging instrument probe. A further problem to be solved by the present invention is the provision of a puncture device guide for use with medical imaging instruments that repeatably allows accurate and safe guidance of a puncture device to locations on and/or in a patient relative to a medical imaging probe. A further problem to be solved by the present invention is the provision of such a device which reduces, minimizes or eliminates the risk of accidentally pushing the device into the endocavity of a patient. A further problem to be solved by the present invention is the provision of such a device which reduces, minimizes or eliminates the risk of contaminating the puncture/injection site, in particular if the device is used for repeated use. A further problem to be solved by the present invention is the provision of such a device which reduces, minimizes or eliminates the need of cleaning (e.g. sterilizing) or replacing the device in between repeated use for the same patient.

The object is solved by the subject-matter defined in the claims.

The present invention is advantageous over the prior art due to reducing the risk of the puncture device guide to accidentally enter endocavities thereby becoming contaminated and/or harming a patient. Further the present invention is advantageous by guiding a puncture device with higher accuracy. Further, the puncture device guide of the present invention has the advantage that it does not get contaminated (e.g., by feces) when a puncture device is used with it that itself gets contaminated during use. Thus, the puncture device guide of the present invention does not have to be replaced or cleaned in between repeated guidance of different puncture devices when used for the same patient. Moreover, the feature of contamination free guidance of puncture devices can be combined with high accuracy of puncture device movement within a patient's tissue. Further the puncture device guide is designed to be especially useful for injection of needles and/or administration of compositions and/or substances into the anal sphincter apparatus for prevention and/or treatment of anal incontinence.

TERMS AND DEFINITIONS

Figure 1:
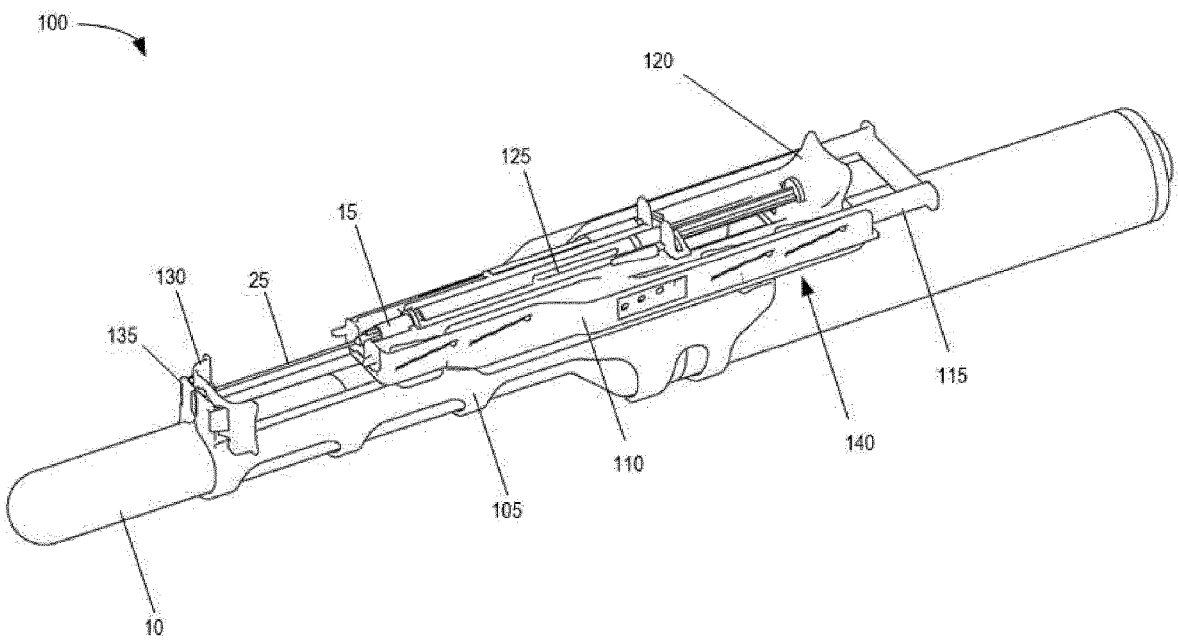
FIG. 1 is an isometric view illustrating one embodiment of a needle guidance device for use with an ultrasound probe, consistent with embodiments described herein.

The term "injection" as used herein, refers preferably to a process comprising introducing an injection device, for instance a needle into a body tissue without initiating an expulsion process yet.

The term "syringe" means generally any fluid delivery device comprising a fluid reservoir (e.g. syringe body with at least one chamber). The syringe body can comprise one or more chambers, which are preferably cylindrical. Each of the chambers is preferably adapted to receive a syringe piston. By displacement of the at least one syringe piston in the syringe body, fluid can be expelled from the syringe body through the syringe needle. The injection syringe can for example comprise a syringe body with a single syringe chamber, to which the syringe needle is connected and in which a syringe piston is arranged. Alternatively, the syringe can comprise two or more chambers, to which the syringe needle is connected and in which preferably in each case a syringe piston is arranged. In a preferred embodiment of the present invention, the syringe additionally is used as an electromyography probe (EMG probe), to conduct electrical signals from the tissue in which the injection takes place.

The term "syringe needle" or "needle" as used herein, refers preferably to devices comprising injection cannulas (hollow syringe needle) attachable to a syringe or inseparably attached to a syringe or a piston device with at least one syringe piston and at least one piston stem. The syringe needle is preferably straight or curved. It can have asymmetric or symmetric bevels of different angles. The syringe needle can be made from one or more materials, such as but not limited to stainless steel.

The term "administering" as used herein, comprises preferably the expulsion of an injection solution releasing a preferably pharmaceutically active substance and/or composition through an injection device into a specific site within the human body, in particular preferred into or adjacent to muscle-tissue providing for anal continence (e.g., anal sphincter apparatus). The administering process can be, but is not limited to, static, i.e., the injection device remains at the position reached. Alternatively, the injection process is dynamic, preferably in that an injection device is retracted from the tissue of a patient during administration of above-mentioned substance. The term "patient" as used herein can interchangeable be used with the term "subject" which preferably refers to a human, an animal, or a mammal.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e., excluding the presence of additional other matter) and "comprising but not consisting of" (i.e., requiring the presence of additional other matter), with the former being more preferred.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items. The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction used in the description of the present application should be construed as critical or essential to the invention unless explicitly described as such. Also, as used herein, the article "a" is intended to include one or more items.

DETAILED DESCRIPTION OF THE EMBODIMENTS

The following detailed description refers to the accompanying drawings. The same reference numbers in different drawings may identify the same or similar elements. Also, the following detailed description does not limit the invention.

Implementations described herein relate to guidance devices for facilitating the placement of a puncture device (e.g., a needle) at a defined position relative to an ultrasound probe. The term "guidance device" as used herein can be used interchangeably with the terms "puncture device guide" or "puncture device guidance devices". Guidance devices described below include components that are adjustable to provide a number of parallel paths relative to each other and at different defined distances from the ultrasound probe. Accordingly, these guidance devices allow for radial translation of the needle path without changing an angle of orientation relative to the ultrasound probe. However, despite the improvements of providing different parallel paths, proper alignment of the needle tip at the point of injections remains a challenge for practitioners.

Consistent with embodiments described herein, a guidance device provides additional support of a needle tip near a needle injection site to maintain a selected path throughout an injection. In some implementations, the additional support may be automatically retracted for simple disposal with the used syringe after an injection. Devices and methods described herein may enable syringe insertion and syringe-needle insertion, respectively, alignment, and removal for multiple different injections (e.g. 2, 3, 4, 5, 6, 7, 8, 9, 10, 11, 12, 13, 14, 15 or more different injections) without removal of an ultrasound probe from the patient. Preferably devices and methods described herein may enable syringe-needle insertion, alignment, and removal for 5-20, more preferably 12 injections.

For example, in one implementation, the ultrasound probe may be a transrectal ultrasound probe and the guidance device may be configured to facilitate guidance of a hypodermic needle to administer medication at a location relative to the ultrasound probe. Consistent with embodiments described herein, the needle guidance device may be adjustable between a plurality of parallel paths while maintaining the angular orientation and axial relationship between the needle and the ultrasound probe. A needle guide is provided to selectively position a distal end of the needle on one of the parallel paths and to maintain alignment of the needle throughout an injection procedure. According to one implementation, the needle guide includes a combination of interacting features on a syringe holder assembly, an adaptor or probe adapter (105), and a needle guide plate. The needle guide plate is positioned at a distal end of the probe adapter to stabilize the needle tip and ensure it is aligned with the axis of the syringe body.

Thus, the present invention provides a puncture device guide, comprising:
an adapter (105) configured to fixedly attach to an ultrasound probe (10);
a syringe holder assembly (140) configured to slidingly attach to the adapter (105) and receive a syringe (15) therein;
wherein the syringe holder assembly (140) is configured to slide on probe adapter (105) in an axial direction relative to the ultrasound probe (10); wherein the syringe holder assembly (140) is configured to allow for selective adjustment of a radial distance for a path of a needle (25) of the syringe (15) relative to the ultrasound probe (10); wherein the adapter (105) includes a tip guide (135, 1135) to selectively align a distal end of the needle (25) with the radial distance for the path; and wherein, when the ultrasound probe (10) is inserted into a patient, the syringe assembly is configured to slide forward on the adapter to insert the needle past the tip guide into a patient. The tip guide (135, 1135) is preferably also useful to stop the syringe holder from entering the endocavity, in particular when attached to an ultrasound transducer. More preferably, the tip guide (135, 1135) is useful to stop the syringe holder from entering the rectal endocavity.

In one embodiment of the present invention, the syringe holder assembly (140) is configured to receive one or multiple syringes (15), preferably 1, 2, 3, 4, 5, 6, 7, 8, 9 10, 11, 12, 13, 14 or 15 syringes, more preferably 12 syringes (15). In one embodiment of the present invention, the syringe holder assembly (140) is configured to receive one or multiple syringe-needles (25), preferably 1, 2, 3, 4, 5, 6, 7, 8, 9, 10, 11, 12, 13, 14 of 15, more preferably 12, wherein the number of syringe-needles is the same, or preferably not the same as the number of syringes (15) received by syringe holder assembly (140). If the number of syringe-needles is not the same as the number of syringes, the syringe comprises preferably 2, 3, 4, 5, 6, 7, 8, 9 10, 11, 12, 13, 14 or 15 adapters to fix each one syringe-needle thereon. Moreover, the syringe is preferably configured in that if all adapters are connected to each one syringe-needle, any fluid in the syringe can be pressed or pulled through all syringe-needles simultaneously and preferably into different locations in the same patient. Alternatively, multiple syringes, preferably 2, 3, 4, 5, 6, 7, 8, 9, 10, 11, 12, 13, 14 or 15, may be configured to be connected to only one syringe-needle. This results in that fluid of different syringes can be pressed or pulled simultaneously or subsequently through one syringe-needle, preferably into the same location in the same patient. Preferably, the number of syringes (15) received by the syringe holder assembly (140) is 1 to 3 and the number of syringe-needles (25) received by the syringe holder assembly (140) is 3 to 12, more preferably 6 to 12 and even more preferably 12. Preferably the syringe holder assembly (140) is configured to receive one syringe (15) and 12 syringe-needles (25).

An example of such a puncture device guide according to the present invention is shown in FIG. 1. FIG. 1 is an isometric view illustrating one embodiment of a needle guidance device 100 for use with an endocavity ultrasound probe 10, consistent with embodiments described herein. As shown, needle guide device 100 includes a probe adapter 105 with a tip guide 135, a body member 110, a slide member 115, a cradle member 120, a syringe cartridge member 125, and a guide plate 130. Body member 110, slide member 115, cradle member 120, and syringe cartridge member 125 may be collectively referred to as a syringe holder assembly 140. Preferably said tip guide 135 is designed in that it prevents the probe 10 from moving deeper into a patient when the tip guide 135 touches the patient. For preventing this, the tip guide 135 preferably has a rectangular or circular shape. Preferably the tip guide 135 has a hole or multiple holes or a gap or a slot to allow a needle or 2, 3, 4, 5, 6, 7, 8, 9, 10, 11, 12, 13, 14, 15, 16, 17, 18, 19 or 20 needles to pass through. More preferably, the hole(s), slot or gap of the tip guide is big enough to let the one or more needle(s) pass though without touching the tip guide. This is important for avoiding a potential contamination of the tip guide. Preferably such slot, gap or hole has a width of about 0 to about 10 mm, more preferably about 2 to about 8 mm, more preferably about 3 to about 5 mm. Preferably, the tip guide has a size in the range of about 0.5 to about 5 cm×about 0.5 to about 5 cm, more preferably about 1 cm×about 1.5 cm or alternatively an area of about 0.25 cm$^2$ to about 25 cm$^2$. The inventors found that a tip guide 135 not only is suitable to align the needle tip within the axis of the ultrasound probe 10, but also allows to stop the device from accidentally enter endocavities such as the rectum during use of the device. If a device would accidentally enter an endocavity, this could lead to a contamination of the device and/or harm of the patient. Thus, the tip guide 135 is especially useful for the device of the present invention when used on a patient.

In an assembled configuration and prior to administration, a hypodermic syringe 15 having a needle 25 may be received within needle guidance device 100 as described below. During use, syringe 15 is inserted into syringe cartridge member 125, which is then inserted into cradle member 120. Slide member 115 is moved to adjust the position of body 110 and syringe 15 relative to the probe 10 so that guide plate 130, with the distal end of needle 25 therein, engages the tip guide 135 of probe adapter 105. Probe 10 may be inserted into a patient's rectum, for example, no farther than tip guide 135. With probe 10 positioned within the patient, slide member 115 is moved further forward and the needle 25 is injected to the patient. If the puncture device guide comprises a guide plate 130 as further described below, with probe 10 positioned within the patient, slide member 115 is moved further forward so that body 110 contacts guide plate 130 and the needle 25 is injected to the patient. The inventors found that syringe needle is to be injected into a patient for about 2 to about 10 cm, more preferably for about 3 to about 6, more preferably for about 5 cm in order to reach the anal sphincter muscle when syringe holder assembly 140 is attached to an ultrasound probe 10. Thus, the distance between the distal end of the syringe-needle 25 and tip guide 135, 1135 is preferably about 2 to about 10 cm, more preferably about 3 to about 6 cm, more preferably about 5 cm. In a preferred embodiment of the present invention, the puncture device guide further comprises a guide plate (130, 1130), the guide plate including: a hole (606) to receive the needle (25) therethrough, a boss (608, 1108) configured to be received by the tip guide (135, 1135), and a coupling element (602) configured to removably attach the guide plate (130, 1130) to the tip guide (135, 1135). In a further preferred embodiment, the guide plate (130, 1130) further comprises multiple holes (606) at different radial distances, wherein each of the multiple holes (606) corresponds to one of the radial distances for the path of the needle (25).

In a preferred embodiment of the present invention, the puncture device guide is configured so that in the assembled configuration and prior to administration, a hypodermic syringe 15 having a needle 25 may be received within needle guidance device 100 as described below. It is preferably further configured in that during use, syringe 15 can be inserted into syringe cartridge member 125, which can then be inserted into cradle member 120. Slide member 115 is preferably configured to be moved to adjust the position of body 110 and syringe 15 relative to the probe 10 so that tip guide 135, 1135 of the probe adaptor is engaged by guide plate 130, with the distal end of needle 25 therein. Probe 10 is preferably configured to be inserted into a patient's rectum, for example, no farther than tip guide 135, 1135. With probe 10 positioned within the patient, slide member 115 is preferably configured to be moved further forward so that body 110 contacts guide plate 130 and the needle 25 can be injected to the patient. Preferably, the puncture device guide is configured in that the needle can be moved through the hole(s), slot or gap of the guide plate. The inventors found that the use of a guide plate as described herein and e.g. shown in FIG. 7. is especially advantageous as the needle thereby is better stabilized i.e. more force is required on the needle tip to result in bending or movement of the needle relative to the axis of the transducer (Example 1, Table 1). Also, the inventors could demonstrate that such guide plate improves the accuracy of a needle when moving through muscle tissue in order to allow more accurately reaching the aimed destination with the needle tip (Example 2, Table 2). Thus, the use of a guide plate 130 is preferably and especially advantageous in order to solve the object of the present invention. Further preferred is the use of a guide plate including one or multiple holes 606 to receive the needle(s) 25 therethrough. Preferably, the guide plate including multiple holes 606 comprises about 2 to about 15 holes, more preferably about 2 to about 10 holes, even more preferably about 2 to about 5 holes. Even further preferred is that the guide plate comprising one or multiple holes 606 contains a boss 608, 1108 configured in a way to be received by the tip guide 135 of the adapter 105. More preferably such guide plate 130 contains a coupling element 602 configured to removably attach the guide plate 130 to the tip guide 135. More preferably, the multiple holes 606 each correspond to selected radial distances for the path of the needle 25. Even more preferably said radial distances are selected in a way that they are about 0.1 to about 10 cm distant from the probe 10, even more preferably about 0.1 to about 5 cm and even more preferably about 0.1 to about 2 cm distant from the probe.

More preferably, said guide plate 130, 1130 comprises a release hole 604 adjacent the coupling element (602), wherein the release hole (604) is configured to receive a tab (360) therein that releases the coupling element (602) from the tip guide (135, 1135). The release hole 604 is preferably able to receive a tab 360 preferably located on the syringe holder assembly 140. Said release hole is configured so that when it receives a tab 360 the coupling element 602 is released form the tip guide 135. Preferably, release of the guide plate 140 by entering of a tab 360 into the release hole 604, leads to attachment of the guide plate 130 to the syringe holder assembly 140. Preferably, the puncture device guide and the guide plate are configured in that the guide plate can be easily changed, in particular during use. Preferably, the puncture device guide and the guide plate are configured in that a new guide plate is used for each injection, i.e. that the guide plate is changeable after each injection.

In a further preferred embodiment, the syringe holder assembly (140) further comprises the tab (360), wherein, if the syringe holder assembly (140) slides forwards on the adapter (105), the tab is inserted into the release hole (604) to release the coupling element (602) and attach the guide plate (130, 1130) to the syringe holder assembly (140). Alternatively in a preferred embodiment of the present invention, the tip guide 1135 further comprises one or multiple holes or slots (1107), more preferably about 2 to about 15, more preferably about 2 to about 10 and even more preferably about 3 to about 5 slots 1107 at different radial distances. Preferably, radial distances are from about 0.5 to about 5 cm, more preferably from about 0.5 to about 2 cm and even more preferably from about 0.5 to about 1 cm. Preferably between the multiple holes is a distance of about 0.1 to about 1 mm. The multiple slots (1107) at different radial distances are preferably configured to receive the boss (1108) of the guide plate (1130). The tip guide 1135 preferably is configured to receive the boss 1108 of the guide plate 1130. More preferably, each of the multiple slots 1107 corresponds to one of the radial distances for the path of the needle. Even more preferably said radial distances are selected in a way that they are about 0.1 to about 10 cm distant from the probe 10, even more preferably about 0.1 to about 5 cm and even more preferably about 0.1 to about 2 cm distant from the probe. An example of such a preferred embodiment is shown in FIGS. 11A-11D.

In a further preferred embodiment of the present invention, the syringe holder assembly (140) is configured to slide backwards on the adapter (105) to retract the needle (25) from the patient and back past the tip guide (135, 1135), wherein, when the syringe assembly (140) slides backwards, the guide plate (130, 1130) stays attached to the tabs.

Engagement of body 110 with guide plate 130 causes guide plate 130 to release from tip guide 135 and attach to body 110. In particular, the guide plate 130, 1130 may be configured in that after it is attached to body 110 and released from tip guide 135, 1135, it is able to slide on the adapter together with the syringe holder assembly (140) as e.g. shown in FIGS. 9A and 9B.

In one embodiment of the present invention, via the cartridge member 125, the syringe barrel 20 is retracted within the cradle member 120 to administer its contents during withdrawal from the patient. Preferably, pulling slide member 115 is resulting in an axial movement of the needle 25 relative to the probe 10 and adapter 105 for up to about 5 cm more preferably up to about 3 cm. Preferably, pulling slide member 115 is resulting in an axial movement of the needle 25 relative to the tip guide 135, 1135 thereby reducing the distance of the distal end of the needle 25 to the tip guide 135, 1135 by about 1 to about 10 cm, more preferably by about 2 to about 6 cm and even more preferably by about 3 cm. The inventors found that this is especially advantageous as by such distance, the whole length of a muscle, preferably the external anal sphincter muscle can be administered with a suspension.

When slide member 115 is pulled completely towards the proximal end of the cradle member 120 (configuration as in FIG. 8B), the distance between the distal end of the needle 25 and tip guide 135, 1135 preferably is about 0.1 cm to about 3 cm, more preferably about 1 cm to about 2 cm and even more preferably about 1.5 cm. The inventors found that such remaining distance between distal needle end and the tip guide is especially advantageous as after administration of a suspension into a patient, the needle stays in the patient when the tip guide is touching the patient, thereby allowing to wait for a reasonable amount of time until administered suspension is completely soaked up by the patient's tissues. This prevents from any reflux of suspension happening through the injection channel outside the patient's body, when the needle is removed from the patient.

In another preferred embodiment of the present invention, the syringe holder assembly 140 is configured to slide backwards on the adapter 105 to retract the needle 25 from the patient and back past the tip guide. Preferably, with guide plate 130 now attached to body 110, slide member 115 is pulled backward (e.g., away from tip guide 135), which pulls needle 25 out of tip guide 135.

Syringe cartridge member 125 can then be released from cradle member 120 and the used syringe 15 and guide plate 130 are simultaneously removed from syringe cartridge member 125.

In another embodiment of the present invention, the syringe holder assembly 140 is configured to slide backwards.

Figure 2A:
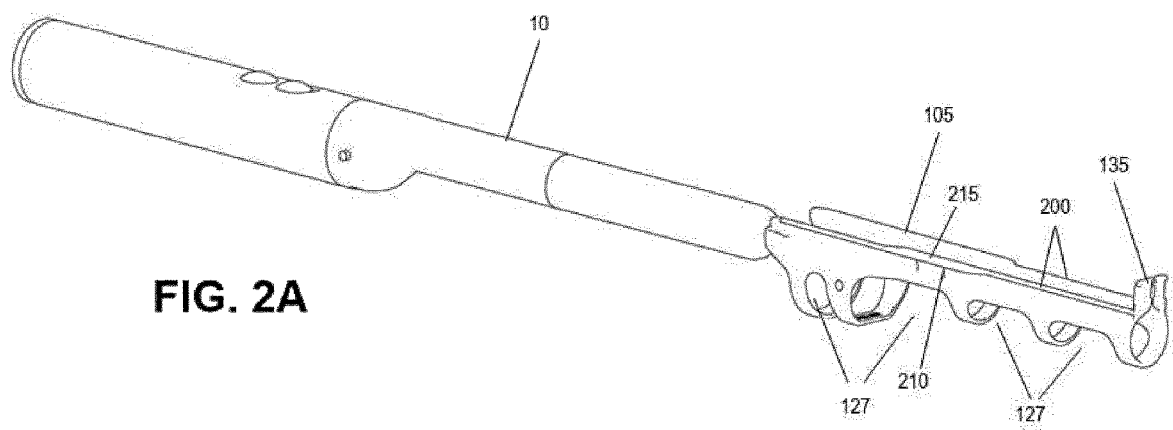
FIGS. 2A and 2B are assembly and isometric views, respectively, illustrating attachment of the probe and probe adapter of FIG. 1.
Figure 2B:
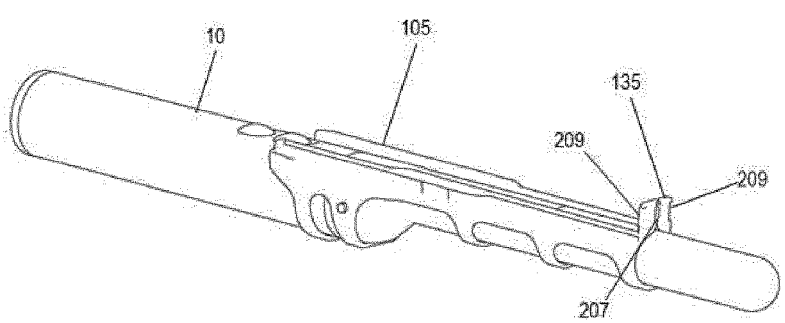

FIGS. 2A and 2B are assembly and isometric views, respectively, of probe 10 and probe adapter 105 of FIG. 1. Consistent with embodiments described herein, probe adapter 105 may include a generally tubular configuration sized and shaped to conform to an outer surface of ultrasound probe 10. Probe adapter 105 may be slid over a distal end of probe 10 and held in place with a friction/interference fit. Probe adapter 105 may be configured to receive and support syringe holder assembly 140. As shown, an upper portion of adapter 105 includes attachment rails 200 that engage corresponding clip elements 315 projecting from a lower surface of body member 110, as shown in FIG. 3A and described in detail below. In one implementation, attachment rails 200 include opposingly oriented ribs or projections 210 that together form a planar upper surface 215 for supporting body member 110 thereon.

As shown in FIGS. 2A and 2B, in one embodiment, adapter 105 includes cutouts 217 for reducing the weight of adapter 105 and for allowing access to controls or ports positioned at various locations on ultrasound probe 10. Consistent with embodiments described herein, adapter 105 may be formed of a plastic or polymeric material and may be manufactured in any suitable manner, such as injection molding, extrusion molding, 3D printing, etc.

Adapter 105 includes tip guide 135 at a distal end. Tip guide 135 may project in a substantially orthogonal plane to a longitudinal axis of probe 10/probe adapter 105. As described further herein, guide plate 130 may be removably clipped to tip guide 135. Tip guide 135 may include a slot 207 through which needle 25 may pass (e.g., during an injection procedure) at a selected parallel path (e.g., a selected radial distance of needle 25 from probe 10).

Although adapter 105 depicted in the Figures illustrates a particular configuration, it should be understood that different configurations may be implemented based on the configuration of the ultrasound probe with which needle guide device 100 is to be used. Furthermore, although not depicted in the Figures, in use, a sterile sheath or other cover may be place on or over ultrasound probe 10 prior to attachment of ultrasound probe 10.

Figure 3:
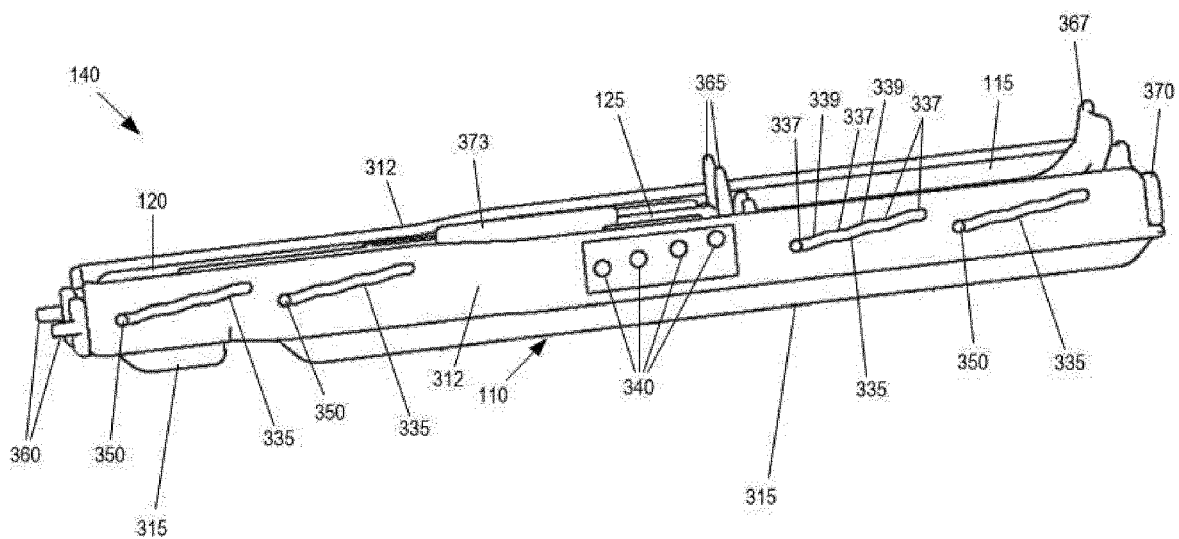
FIG. 3 is an isometric view illustrating the syringe holder assembly of FIG. 1.

FIG. 3 is an isometric view illustrating syringe holder assembly 140. As shown in FIG. 3, body member 110 includes a generally frame-like structure with longitudinal sides 312 that receives and supports slide member 115, cradle member 120, and syringe cartridge member 125. Syringe holder assembly 140 is described further in connection with the subsequent Figures.

Figure 4A:
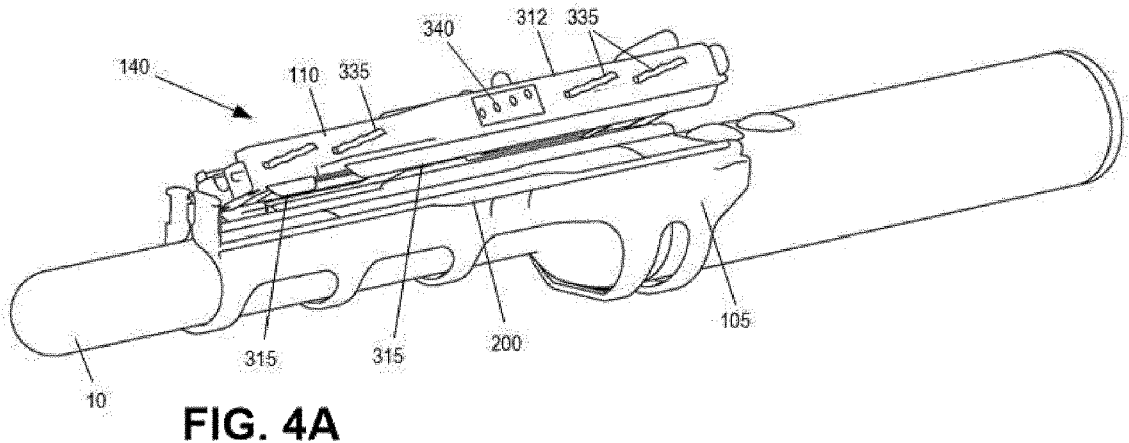
FIGS. 4A and 4B are side and rear isometric views illustrating attachment of the syringe holder assembly and probe adapter of FIG. 1.
Figure 4B:
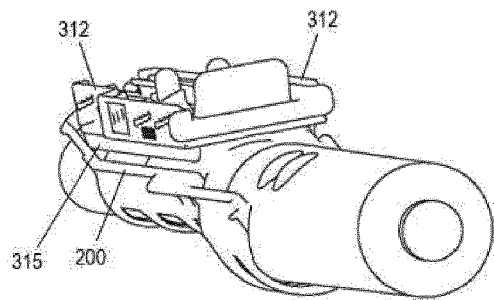

FIGS. 4A and 4B are side and rear isometric views, respectively, illustrating attachment of syringe holder assembly 140 to probe adapter 105. As shown in FIGS. 3, 4A and 4B, body member 110 may further include a plurality of clip elements 315 on a bottom portion of both longitudinal sides 312. Clip elements 315 are spaced to engage attachment rails 200 on adapter 105. In particular, each clip element 315 may include a barb member or indent configured to engage a portion of the underside of attachment rail to secure syringe holder assembly 140 to adapter 105 while allowing for longitudinal positioning of syringe holder assembly 140 relative to ultrasound probe 10.

In one implementation, during assembly as shown in FIGS. 4A and 4B, a downward force is placed on body member 110, which causes clip elements 315 to engage an edge portion of attachment rails 200. Continued downward force, causes clip element 315 to splay outwardly, allowing barb members or indents of clip element 315 to slide over and fully engage attachment rails 200. In other implementations, clip elements 315 may not include barb members, but may rather include non-angled inward projections. In such an embodiment, body member 110 may be longitudinally slid onto attachment rails 200 during assembly.

As shown in FIGS. 3, 4A, and 4B, longitudinal sides 312 may include a plurality of path adjustment channels 335 and path selection apertures 340. In the illustrated embodiment, body member 110 includes four opposing pairs of path adjustment channels 335 and four opposing pairs of path selection apertures 340. In other implementations, more or fewer path adjustment channels 335 and/or path selection apertures 340 may be used. Furthermore, although pairs of channels 335 and apertures 340 are described for corresponding longitudinal sides 312, in some implementations, channel(s) 335 and/or aperture(s) 340 may be provided on only one side or on alternate sides of body member 110.

Consistent with embodiments described herein, each of path adjustment channels 335 forms a generally angled channel having a plurality of planar portions 337 and angled portions 339 corresponding to a number of possible path positions. In the illustrated embodiment, each path adjustment channel 335 includes four planar portions 337 and three angled portions 339 provided between each planar portion 337. Although not restricted herein, in one implementation, a vertical distance between a bottom of a first (e.g., lowest) planar portion 337 and a bottom of a fourth (e.g., highest) planar portion 337 is in the range of about 0 to about 10 centimeters (cm), more preferably about 0.5 to about 5 cm and even more preferably about 0.5 to about 1.5 cm. In the same exemplary embodiment, the longitudinal distance between the center of first planar portion 337 and the center of fourth planar portion 337 is in the range of about 0 to about 15 cm, more preferably about 2 to about 15 cm and even more preferably about 5 to about 12 cm. Each of path adjustment channels 335 is configured to receive corresponding selection pin 350 of slide member 115 to thus restrict the movement of slide member 115 to those positions defined by path adjustment channels 335.

Path selection apertures 340 are spaced and positioned to correspond to planar portions 337 in path adjustment channels 335. As described below, one of path selection apertures 340 is configured to receive a corresponding portion of slide member 115 to positively retain slide member 115 in the positioned defined by one of planar portions 337 and prevents inadvertent movement along path adjustment channel(s) 335 during use.

As shown in FIG. 3, a portion of cradle member 120 extends through an opening at the front of body member 110 (e.g., between longitudinal sides 312). More specifically, tabs 360 of cradle member 120 extend past a front end of body member 110 and are configured to engage guide plate 130 in the manner described below. By sliding slide member 115 relative to body member 110 selection pins 350 may be positioned at different planar portions 337 of path adjustment channels 335. For example, a handle 370 of slide member 115 may be pushed or pulled to change the position of selection pins 350, which, correspondingly, changes the parallel path (e.g., distance above attachment rails 200) provided by cradle member 120 and tabs 360.

Figure 5A:
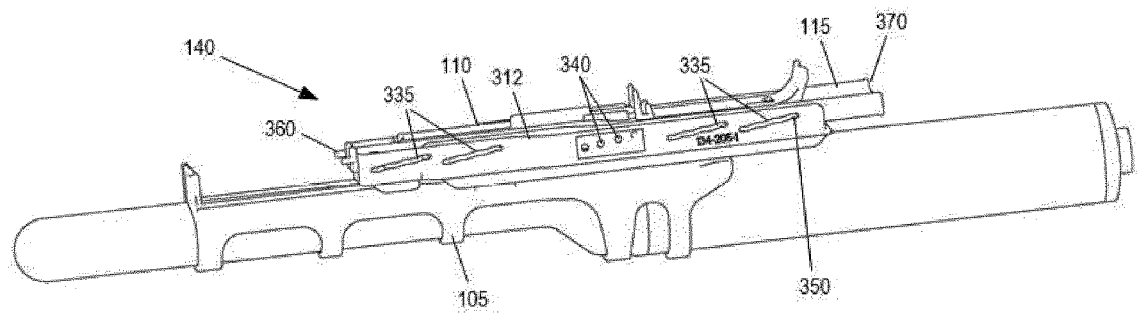
FIGS. 5A and 5B are isometric views illustrating the syringe holder assembly of FIG. 3 in raised and lowered configurations, respectively, relative to the probe adapter of FIG. 2B.
Figure 5B:
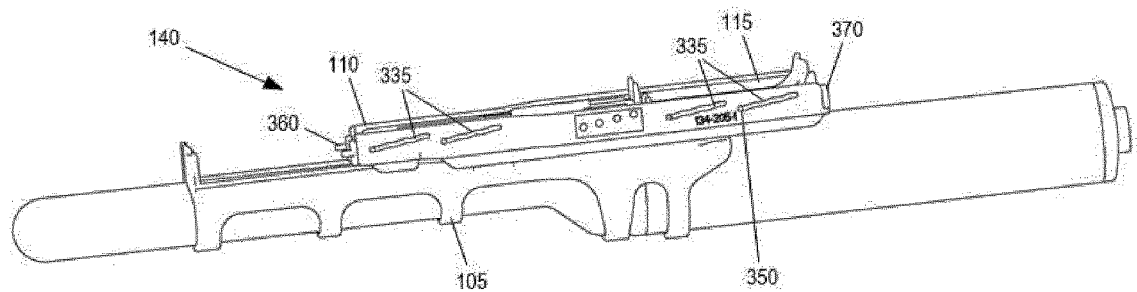

FIGS. 5A and 5B are isometric views illustrating syringe holder assembly 140 in raised (e.g., highest) and lowered (e.g., lowest) parallel path configurations, respectively, relative to probe adapter 105. Syringe holder assembly 140 can position a syringe 15 with needle 25 at any one of multiple distances from the ultrasound probe to provide an injection path parallel to a longitudinal axis of probe 10. As described above, a practitioner may select a parallel path for a particular application/patient.

Figure 6A:
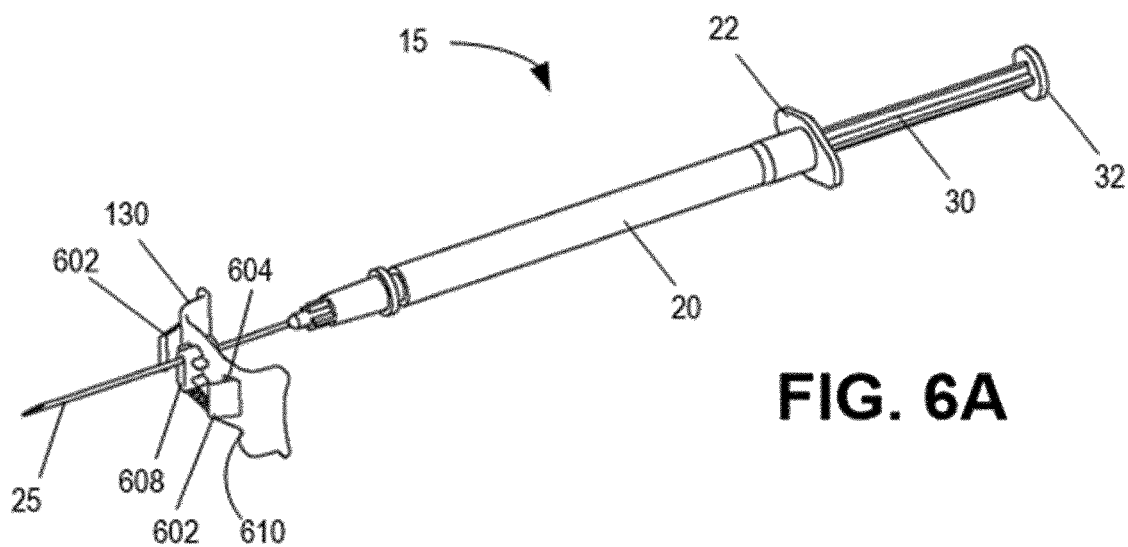
FIGS. 6A and 6B are side and rear isometric views illustrating a syringe engaged with the needle guide plate of FIG. 1.
Figure 6B:
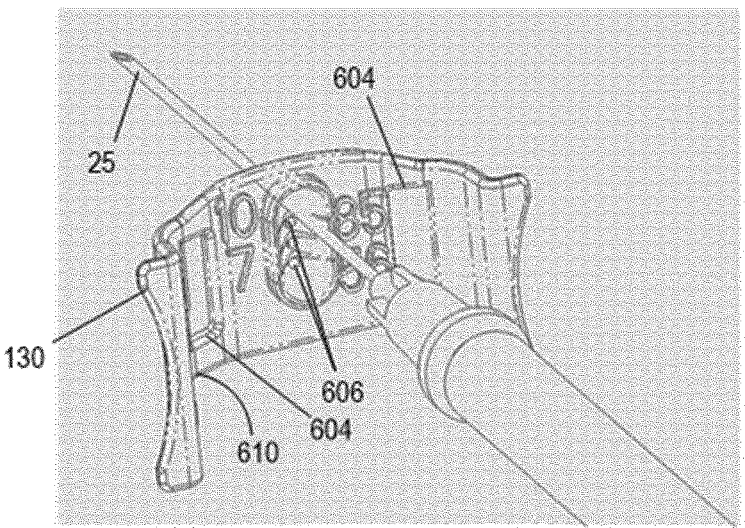

FIGS. 6A and 6B are side and rear isometric views illustrating syringe 15 engaged with needle guide plate 130. Syringe 15 may include a syringe barrel 20, a barrel flange 22, needle 25, a plunger 30, and a plunger flange 32. Needle guide plate 130 may include attachment clips 602 or other coupling elements each adjacent to a release hole 604. Guide plate 130 may also include a set of tip height selection holes 606, a plate alignment boss 608, and a set of rail alignment grooves 610.

The number of tip height selection holes 606 may correspond to the number of different planar portions 337 that may be selected using path adjustment channels 335 on body member 110. Each tip height selection hole 606 is configured to guide needle 25 on a particular parallel path. That is, the radial spacing between each of the tip height selection holes 606 (e.g. relative to probe 10) may correspond to the radial distance between different planar portions 337 such that needle 25 is assured of a parallel path to probe 10 when a needle 25 is inserted through a tip height selection hole 606 that corresponds to one of planar portions 337. According to an implementation, a practitioner may insert needle 25 through a chosen tip height selection hole 606 prior to inserting syringe 15 into syringe holder assembly 140.

Figure 7A:
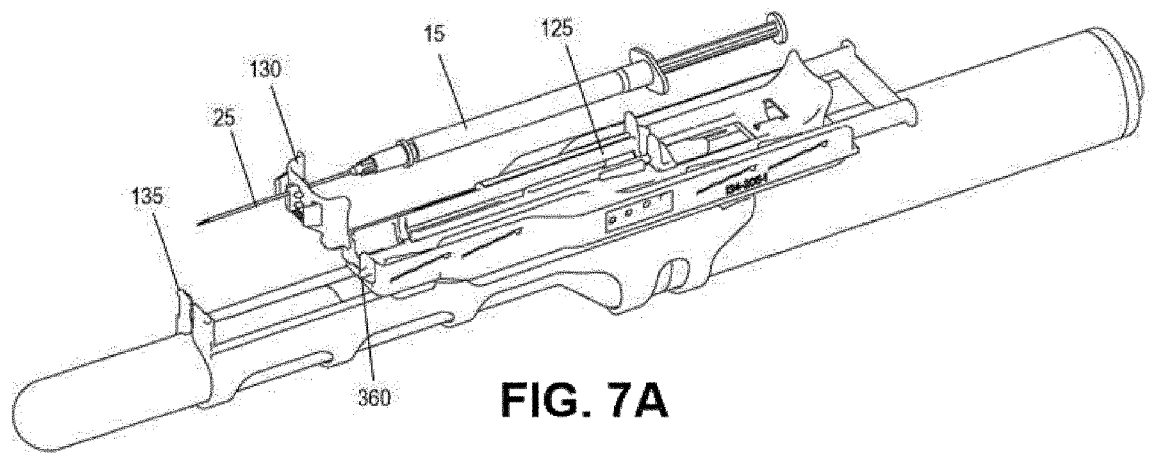
FIGS. 7A-7C are isometric views illustrating the attachment of the syringe and needle guide plate of FIGS. 6A and 6B with the syringe holder assembly and probe adapter of FIG. 5A.
Figure 7B:
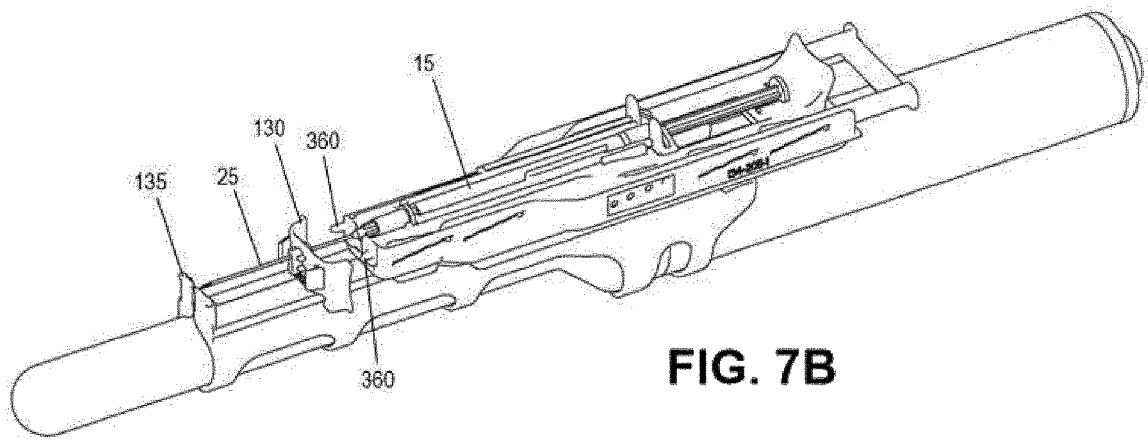

FIGS. 7A and 7B are isometric views illustrating the attachment of syringe 15 and needle guide plate 130 with the syringe holder assembly 140 and probe adapter 105. As shown in FIG. 7A, syringe 15 and guide plate 130 may be inserted into syringe holder assembly 140 simultaneously, with needle 25 extending through guide plate 130.

As shown in FIG. 7B, syringe 15 may be inserted into syringe cartridge member 125. When syringe 15 is inserted into syringe cartridge member 125, the tip of needle 25 is positioned adjacent tip guide 135 with guide plate 130 on needle 25 between body member 110 and tip guide 135. When syringe 15 is in syringe cartridge member 125, rail alignment grooves 610 of guide plate 130 may fit around rails 200 of probe adapter 105.

Figure 7C:
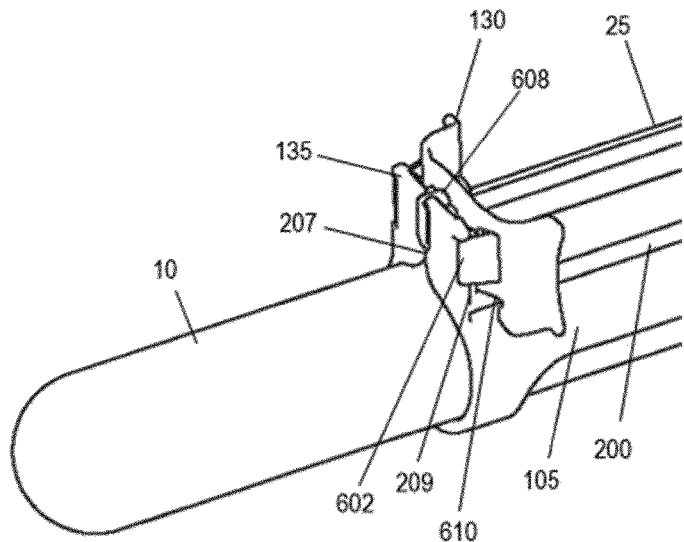

After syringe 15 and guide plate 130 are attached to syringe holder assembly 140, guide plate 130 may be slid longitudinally forward (e.g., by a practitioner) along needle 25 until guide plate 130 engages with tip guide 135, as shown in FIGS. 1 and 7C. Plate alignment boss 608 may be configured to fit into slot 207 of tip guide 135. Plate alignment boss 608 may pass through slot 207 of tip guide 135 in a manner that prevents needle 25 from contacting tip guide 135 during insertion and retraction. According to an implementation, attachment clips 602 may be configured to clip onto adapter 105 when plate alignment boss 608 is inserted through slot 207. More specifically, clips 602 may be configured to align with opposing edges 209 of tip guide 135 when plate alignment boss 608 is inserted into slot 207 of tip guide 135.

Figure 8A:
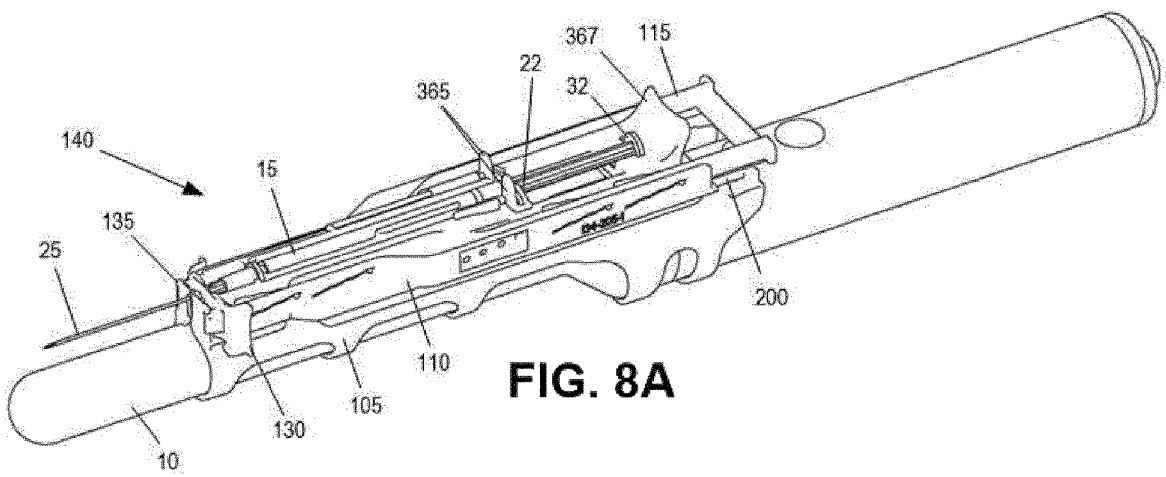
FIGS. 8A and 8B are isometric views illustrating positions of the needle guidance device and syringe during an injection.
Figure 8B:
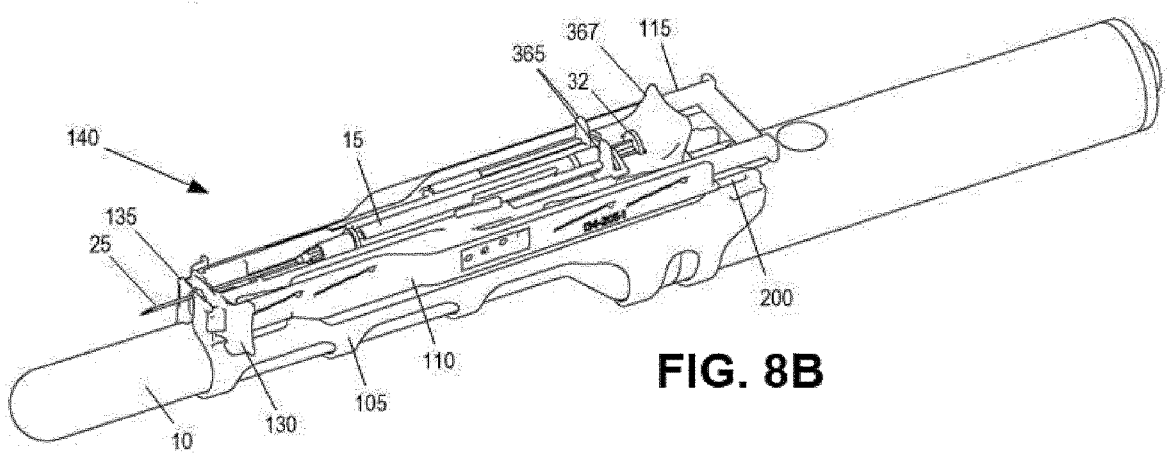

FIGS. 8A and 8B are isometric views illustrating positions of needle guidance device 100 and syringe 15 during an injection. With probe 110 inserted into a patient preferably until tip guide 135 is touching the skin of the patient, syringe holder assembly 140 may be pushed longitudinally forward along attachment rails 200 from the orientation shown in FIGS. 1 and 7C to the orientation shown in FIG. 8A. The forward movement of syringe holder assembly 140 causes needle 25 to pass through guide plate 130, beyond tip guide 135, and into the patient, thereby reaching an injection depth of the needle into the patient of up to about 10 cm, more preferably up to about 7 cm even more preferably of about 4 to about 5 cm. When syringe holder assembly 140 is moved completely forward, tabs 360 of cradle member 120 are inserted into release holes 604 of guide plate 130. Passing beyond holes 604, each of tabs 360 is inserted between an edge 209 and an attachment clip 602, pushing away (e.g., outward) the attachment clips 602 adjacent to each of release holes 604 and causing attachment clips 602 to disengage from tip guide 135. While causing clips 602 to detach from tip guide 135, insertion of tabs 360 into release holes 604 also causes tabs 360 to hold/grip guide plate 130.

With needle 25 in the patient, a practitioner may apply opposing forces to (e.g., squeeze) projections 365 and syringe retraction support 367. As shown in FIG. 8B, projections 365 may move longitudinally backward toward syringe retraction support 367. Force on projections 365 force barrel flange 22 back toward plunger flange 32, causing barrel 20 to retract and release its contents through needle 25 as needle 25 is withdrawn from the patient.

Figure 9A:
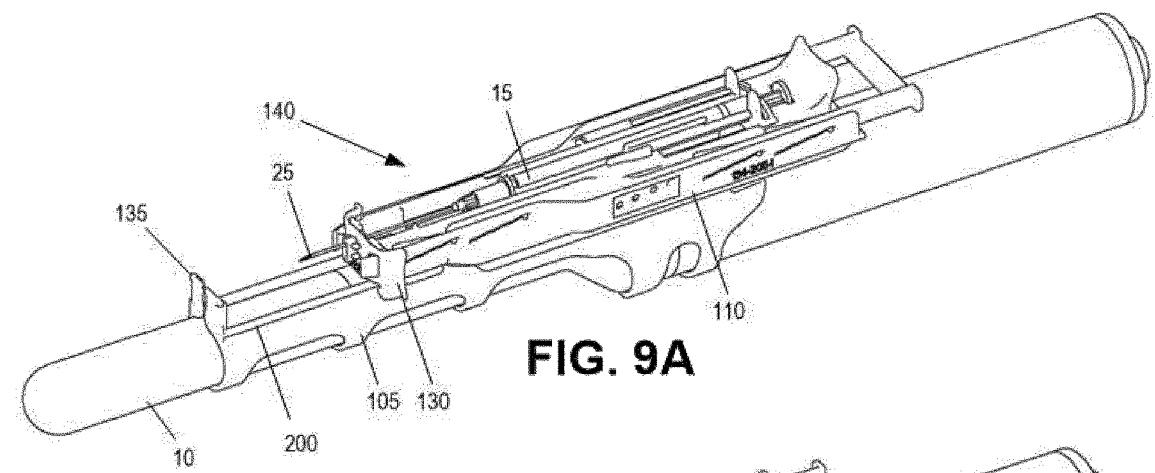
FIGS. 9A and 9B are isometric views illustrating retracted position of the needle guidance device and syringe following an injection.
Figure 9B:
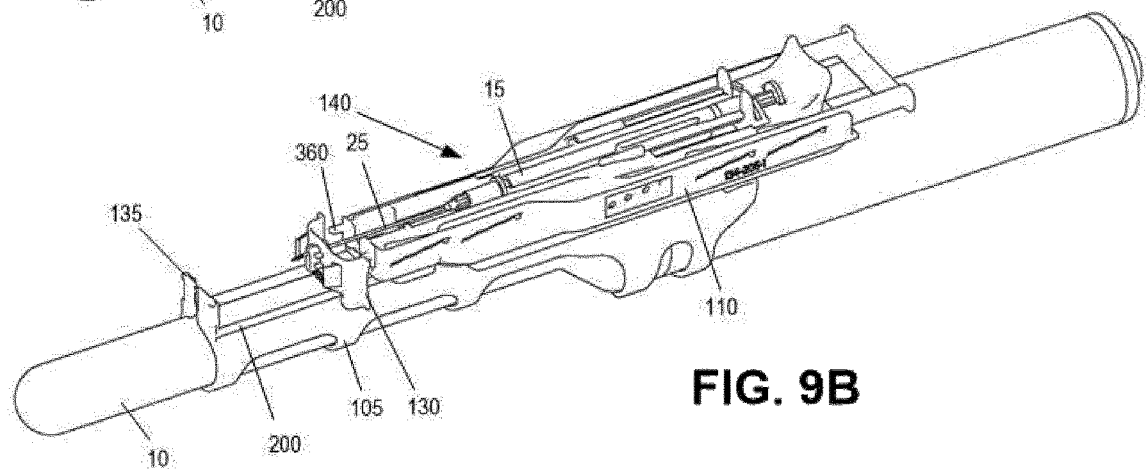

FIGS. 9A and 9B are isometric views illustrating a retracted position of needle guidance device 100 and syringe 15 following an injection. Upon completion of an injection, a practitioner may slide syringe holder assembly 140 longitudinally backwards on attachment rails 200 (e.g., while probe 10 remains within the patient). Guide plate 130, due to engagement with tabs 360, is retracted with syringe holder assembly 140.

After retraction of syringe holder assembly 140 and guide plate 130, guide plate 130 can be pushed longitudinally forward to detach guide plate 130 from tabs 360 and syringe holder assembly 140, as shown in FIG. 9B. For example, a practitioner may gently grip sides of guide plate 130 to flex guide plate 130 and release tabs 360 from release holes 604.

According to an implementation, guide plate 130 may remain resting on a distal portion of needle 25.

Figure 10A:
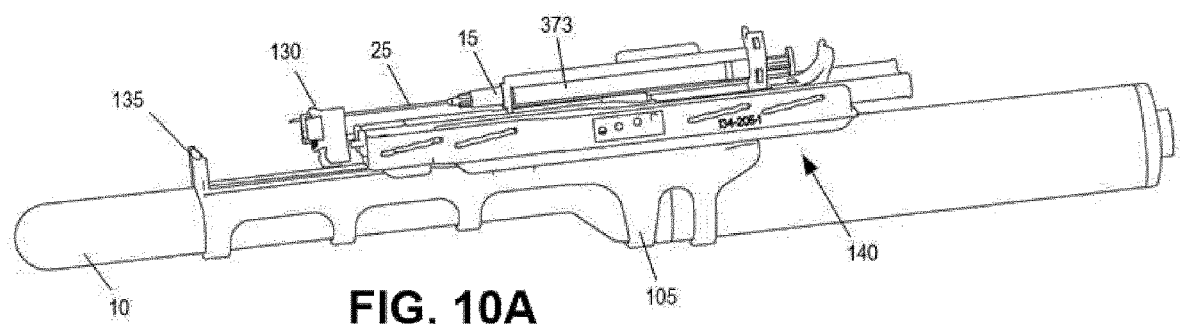
FIGS. 10A-C are isometric illustrations of the ejector body mechanisms during ejection of the syringe from the needle guidance device of FIG. 1.
Figure 10B:
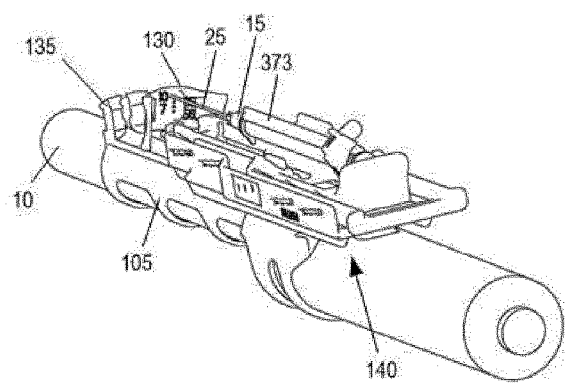
Figure 10C:
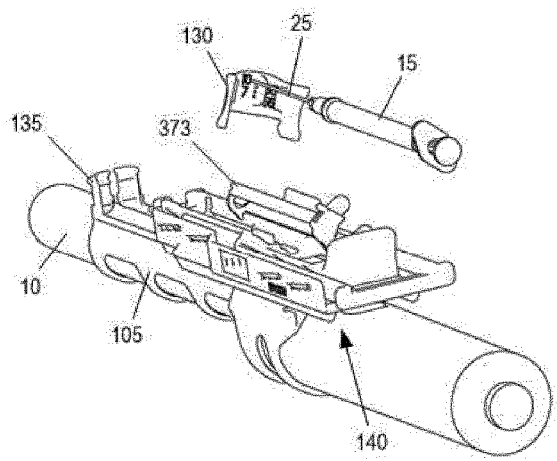

FIGS. 10A-C are isometric illustrations of the ejector body mechanism of syringe cartridge member 125 during ejection of syringe 15 from the needle guidance device 100. Release member 373 of syringe cartridge member 125 may be lifted (e.g., by a practitioner), causing syringe cartridge member 125 to rotate out syringe 15 out of cradle member 120, as shown in FIGS. 10A and 10B. With syringe cartridge member 125 in the raised position, a practitioner has unobstructed access to plunger flange 32 and/or barrel 20 of syringe 15, which may be grasped and removed from syringe holder assembly 140 with guide plate 130 still connected to needle 25, as shown in FIG. 10C. Thus, syringe 15 and guide plate 130 may be removed and discarded without a practitioner contacting contaminated portions of syringe 15 or guide plate 130.

Figure 11A:
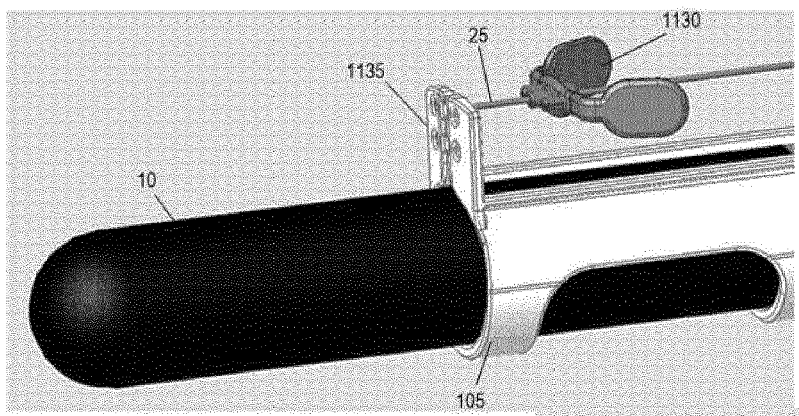
FIGS. 11A and 11B are side and rear perspective views illustrating alignment of another embodiment of a needle guide plate and probe adapter.
Figure 11B:
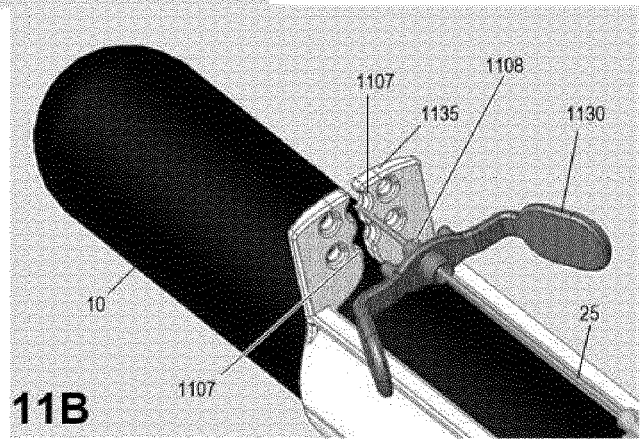

FIGS. 11A-11D are isometric views illustrating another embodiment of a probe adapter and a needle guide plate. FIGS. 11A and 11B show side and rear perspective views of a guide plate 1130 installed on needle 25 of syringe 15, similar to the arrangement described above in connection with FIGS. 7A and 7B. Similar to the description above, the combination of syringe 15 and guide plate 1130 may be inserted into syringe holder assembly 140 simultaneously, with needle 25 extending through guide plate 1130 and the distal end of needle 25 adjacent to tip guide 1135 of probe adapter 1105.

In contrast with guide plate 130 described above, guide plate 1130 may include only one hole 1106 configured to receive needle 25. Tip guide 1135 includes two or more slots 1107 at different heights configured to receive plate alignment boss 1108. Each of slots 1107 may correspond to one of the selectable parallel paths described above in connection with, for example, FIG. 3. Thus, although only two slots 1107 are shown in FIGS. 11A-11D, in other implementations tip guide 1135 may include more than two slots 1107.

Figure 11C:
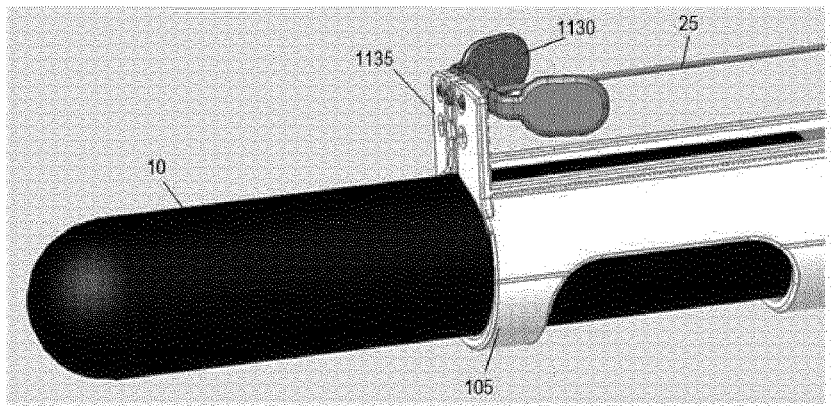
FIGS. 11C and 11D are side and rear perspective views illustrating engagement of the needle guide plate and probe adapter of FIGS. 11A and 11B.
Figure 11D:
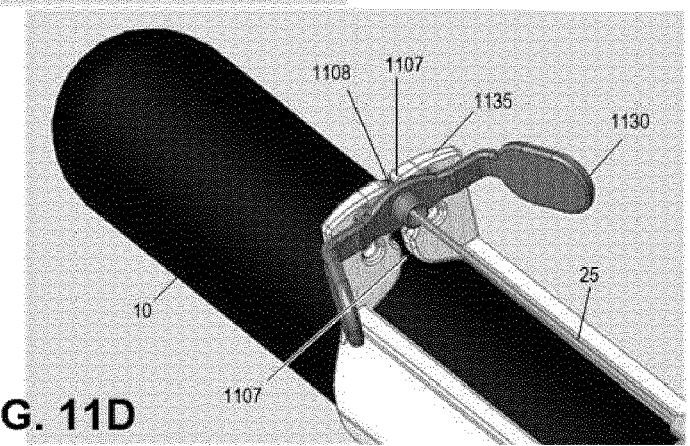

FIGS. 11C and 11D show side and rear perspective views of a guide plate 1130 attached to tip guide 1135, similar to the arrangement described above in connection with FIGS. 1 and 7C. After syringe 15 and guide plate 1130 are attached to syringe holder assembly 140, guide plate 1130 may be slid longitudinally forward (e.g., by a practitioner) along needle 25 until guide plate 1130 engages with tip guide 1135, as shown in FIGS. 11C and 11D. Plate alignment boss 1108 may be configured to fit into a selected slot 1107 of tip guide 1135. According to one implementation, selection of a particular parallel path for syringe holder assembly 140 may align needle 25 and guide plate 1130 with a corresponding slot 1107 of tip guide 1135.

According to one implementation, the system and methods described herein may be used to perform multiple injections in a radial pattern. After a first injection (e.g., as described above), while probe 10 remains in the patient, the radial insertion distance of syringe holder assembly 140 may be adjusted (e.g., as described above in connection with FIGS. 5A and 5B), if necessary. A new syringe 15 and guide plate 130 combination may be inserted into syringe holder assembly 140 (as described in FIGS. 7A-7C), and probe 10 may be rotated to a preferred next injection orientation for the patient, and a second or subsequent injection may be performed using the process described above. Preferably, a new guide plate 130 is used for each new injection.

The present invention also provides a method of performing an injection, the method comprising:

(a) attaching a probe adapter (140) to an ultrasound probe (10), wherein the probe adapter (105) includes a tip guide (135, 1135) at a distal end;

(b) attaching a syringe holder assembly (140) to the probe adapter (140), wherein the syringe holder assembly is longitudinally slidable relative to the probe adapter (140);

(c) inserting the ultrasound probe (10) into a patient;

(d) adjusting the syringe holder assembly (140) to provide a selected radial distance for a syringe needle (25) from the ultrasound probe (10);

(e) inserting the syringe (15) into the syringe holder assembly (140) and aligning a syringe needle (25) with the tip guide (135, 1135);

(f) sliding the syringe holder assembly (140) distally to push the needle past the tip guide (135, 1135) and into the patient;

(g) sliding the syringe holder assembly (140) back to retract the needle (25) from the patient, and (h) removing the syringe (15) from the syringe holder assembly (140).

Preferably, inserting the syringe (15) into the syringe holder assembly (140) further comprises (i) providing a guide plate (130, 1130) with a boss (608, 1108) configured to be received by the tip guide (135, 1135) and a coupling element (602) configured to removably attach the guide plate (130, 1130) to the tip guide (135, 1135); (ii) inserting the syringe needle (25) through a hole (606) in the guide plate (130, 1130), and (iii) inserting the syringe (15) into the syringe holder assembly (140) after inserting the syringe needle (25) through the hole (606). Preferably, inserting the syringe (15) into the syringe holder assembly (140) further comprises selecting the hole from multiple holes (1107) in the tip guide (1135), wherein each of the multiple holes (1107) correspond to a different radial distance for the syringe needle (25) from the ultrasound probe (10). Preferably, inserting the syringe (15) into the syringe holder assembly (140) further comprises sliding the guide plate (130, 1130) along the syringe needle (25) until the guide plate (130, 1130) attaches to the tip guide (135, 1135). Preferably, the guide plate (130, 1130) is slid along the syringe needle (25) until the guide plate (130, 1130) attaches to the tip guide (135, 1135). This may further comprise the step of moving the guide plate (130, 1130) to engage the boss (608, 1108) with one of multiple slots on the tip guide (135, 1135), wherein each of the multiple slots correspond to a different radial distance for the syringe needle (25) from the ultrasound probe (10).

Preferably, when sliding the syringe holder assembly (140) back to retract the needle (25) from the patient, the syringe needle (25) does not contact the tip guide (135, 1135), in particular for avoiding any potential contamination of the tip guide (135, 1135).

Preferably, if the syringe holder assembly (140) is slid distally to push the needle (25) past the tip guide (135, 1135) and into the patient, the syringe holder assembly (140) engages the guide plate (130, 1130) and release the guide plate (130, 1130) from attachment to the tip guide (135, 1135). More preferably, when sliding the syringe holder assembly (140) back to retract the needle (25) from the patient, the syringe holder assembly (140) retracts the guide plate (130, 1130) away from the tip guide (135, 1135).

In a preferred embodiment of the method according to the present invention the method further comprises the step of detaching the guide plate (130, 1130) from the syringe holder assembly (135, 1135) by sliding the guide plate (130, 1130) distally along a portion of the syringe needle (25).

Preferably, the step of removing the syringe (15) from the syringe holder assembly (140) of the method according to the present invention further comprises removing the syringe (15) and the guide plate (130, 1130) while the syringe needle (25) remains inserted through the guide plate (130, 1130).

Preferably, the method according to the present invention is performed by any puncture device according to the present invention. Moreover, the puncture device according to the present invention is preferably configured to be used in a method according to the present invention.

Figure 12:
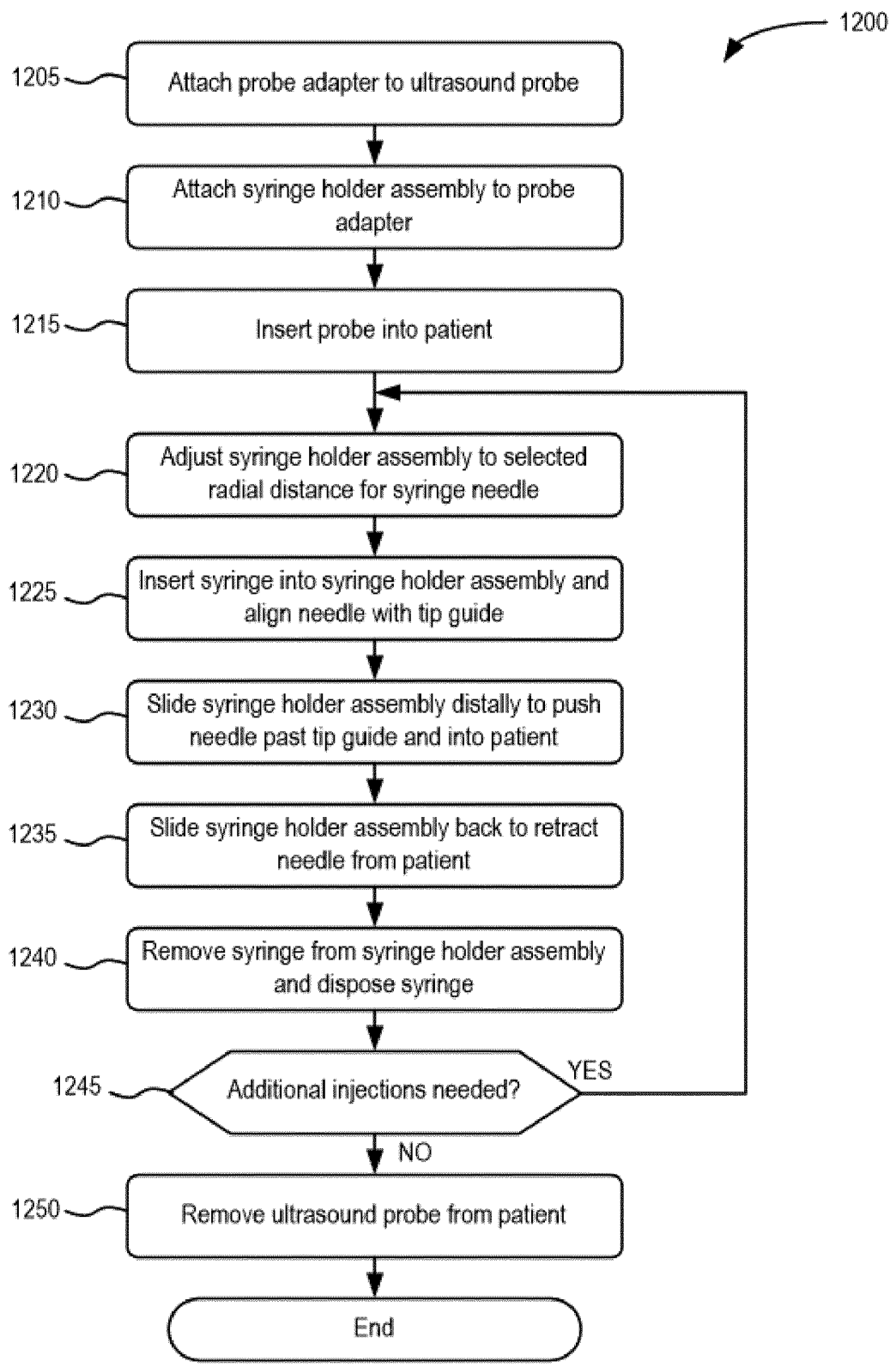
FIGS. 12 and 13 are flow diagrams of an exemplary process for performing injections using a parallel path puncture device guide accordingly to implementations described herein.

FIG. 12 is a flow diagram of an exemplary process for performing injections using a parallel path puncture device guide, according to an implementation described herein. As shown in FIG. 12, process 1200 may include attaching a probe adapter to an ultrasound probe (block 1205) and attaching a syringe holder assembly to the probe adapter (block 1210). For example, as described above in connection with FIGS. 2A-4B, probe adapter 105 may be secured to probe 10 and syringe holder assembly 140 may be clipped to rails 200 of probe assembly 105.

Process 1200 may also include inserting the probe into a patient (block 1215), and adjusting the syringe holder assembly to a selected radial distance for the syringe needle (block 1220). For example, as described above in connection with FIGS. 5A and 5B, a handle 370 of slide member 115 may be pushed or pulled to change the position of selection pins 350, which, correspondingly, changes the parallel path (e.g., a radial distance above attachment rails 200) that cradle member 120 defines for syringe 15.

Process 1200 may further include inserting a syringe into the syringe holder assembly and aligning a syringe needle with a tip guide (block 1225). For example, according to one embodiment, block 1225 may include the steps of FIG. 13 described below. In one preferred embodiment of the present invention, the syringe to be inserted into the syringe holder contains a composition and/or substance. More preferably, the syringe contains a pharmaceutically active composition such as e.g., a suspension of cells. In a preferred embodiment, sliding the syringe cartridge (125) inserted with a syringe (15), filled with a substance or composition, back, results in simultaneously administering the substance or composition into the patient. Preferably, such substance or composition is aimed to be administered into the patient by conduction of the process 1200. In another example, as described in connection with FIGS. 11A-11D, a practitioner may insert needle 25 through a selected hole 1106 of guide plate 1130, insert syringe 15 into syringe holder assembly 140, and then attach guide plate 1130 to a selected slot 1107 of tip guide 1135. In still another implementation, tip guide 1135 may include multiple holes that correspond to the parallel paths for which syringe holder assembly is adjusted, and needle 25 may be inserted through a selected hole of tip guide 1135.

Process 1200 may additionally include sliding the syringe holder assembly distally to push the needle past the tip guide and into the patient (block 1230), and sliding the syringe holder assembly back to retract the need from the patient (block 1235). For example, as described above in connection with FIGS. 8A-9B, with probe 110 inserted into a patient, syringe holder assembly 140 may be pushed longitudinally forward along attachment rails 200. The forward movement of syringe holder assembly 140 causes needle 25 to pass through guide plate 130, beyond tip guide 135, and into the patient. With needle 25 in the patient, a practitioner may squeeze projections 365 and syringe retraction support 367, causing syringe 15 release or administer its contents through needle 25. Preferably thereby projections 365 move for a defined length toward retraction support 367 to cause a movement of the needle 25 relative to the transducer. Such length preferably is about 2 to about 10, more preferably about 2 to about 5, even more preferably about 3 cm long. Upon completion of the injection, a practitioner may slide syringe holder assembly 140 longitudinally backwards on attachment rails 200, while probe 10 remains within the patient.

Process 1200 may further include removing the syringe from the syringe holder assembly and disposing the syringe (block 1240). For example, syringe cartridge member 125 may rotate to lift syringe 15 out of cradle member 120, as shown in FIGS. 10A and 10B. With syringe cartridge member 125 in the raised position, a practitioner may grasp plunger flange 32 and/or barrel 20 of syringe 15 to remove syringe 15 from syringe holder assembly 140 with guide plate 130 still connected to needle 25, as shown in FIG. 10C. Thus, syringe 15 and guide plate 130 may be removed and disposed of without a practitioner contacting soiled portions of syringe 15 or guide plate 130.

Process 1200 may also include determining if additional injections are needed (block 1245). If no additional injections for the patient are needed (block 1245—No), process 1200 may include removing the ultrasound probe from the patient (block 1250). If additional injections for the patient are needed (block 1245—Yes), process 1200 may return to process block 1220 to perform another injection with a new syringe and guide plate, if necessary.

Figure 13:
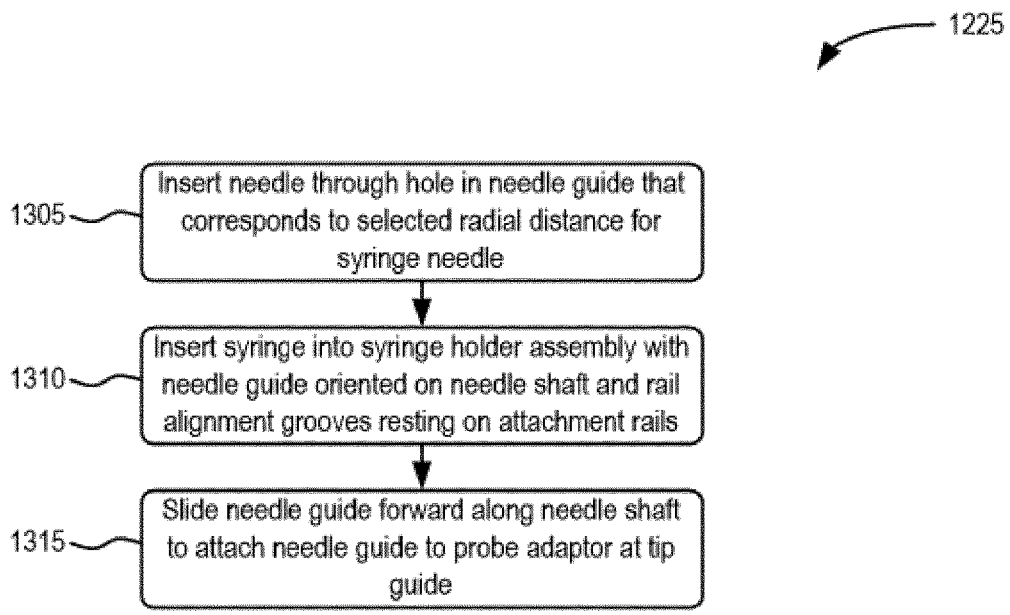

Referring to FIG. 13, process block 1225 may include inserting a needle through a hole, in a needle guide, that corresponds to selected radial distance for the syringe needle (block 1305), inserting the syringe into a syringe holder assembly with the needle guide oriented on the needle shaft and rail alignment grooves resting on the attachment rails of the probe adaptor (block 1310), and sliding the needle guide forward along the needle shaft to attach the needle guide to the probe adaptor at the tip guide (block 1315). For example, before inserting syringe 15 into syringe holder assembly 140, a practitioner may insert needle 25 through a selected hole 606 of guide plate 130, so that the selected hole 606 corresponds to the parallel path to which syringe holder assembly 140 is adjusted. As described in connection with FIGS. 6A-7C, the practitioner may insert syringe 15 into syringe holder assembly 140, with guide plate 130 resting on attachment rails 200, and slide guide plate 130 forward to attach to tip guide 135 of probe holder 105.

Implementations described herein provide a guidance device for facilitating the placement of a puncture device (e.g., a needle) at a defined position relative to an ultrasound probe. Preferably, a substance and or composition can be administered into a patient through the puncture device (e.g. needle). The guidance device provides additional support of a needle tip near the needle injection site to maintain a selected path throughout an injection. The additional support is automatically retracted for simple disposal with the used syringe after an injection. The guidance device minimizes contact of soiled components and enables syringe insertion, alignment, and removal for multiple different injections without removal of an ultrasound probe from the patient.

The foregoing description of implementations provides illustration and description but is not intended to be exhaustive or to limit the invention to the precise form disclosed. Modifications and variations are possible in light of the above teachings or may be acquired from practice of the invention. For example, while a series of blocks have been described with regard to FIG. 12, the order of the blocks may be modified in other embodiments. Further, non-dependent blocks may be performed in parallel.

In one embodiment of the present invention, the puncture device guide is suitable for medical use. Medical use herein refers to a use comprising preventing and/or treating a disease in a subject, preferably a human, an animal, or a mammal. Preferably the medical use comprises preventing and/or treating urinary incontinence, anal incontinence, overactive bladder, underactive bladder, anal fistula(s), hemorrhoids, (chronic) inflammation, myopathies, neuropathies, and/or prostate malignancies. More preferably the medical use refers to a use in preventing and/or treating anal incontinence, more preferably urge fecal incontinence and/or passive fecal incontinence. In order to allow medical use of a device, such device preferably is sterile when it is used. Therefore, the device is preferably designed to be sterilizable prior to use. Preferably such sterilization is performed by use of ethylene oxide, moist heat, dry heat, radiation, vaporized hydrogen peroxide, chlorine gas, vaporized peracetic acid and/or nitrogen dioxide. Thus, the device is preferably made of sterilizable material such as steel, ceramic, and/or plastic. Even more preferably the device is made of sterilizable material comprising plastic, more preferably a terpolymer, even more preferably acrylnitril-butadien-stryol-copolymer. Also preferred is that the material the device is made of is biocompatible. Biocompatible as used herein refers to preferably meeting specifications of ISO 10993-1:2018, more preferably meeting specifications for contact with intact skin and/or intact mucosa as defined in ISO 10993-1:2018. Preferably material of the device according to the present invention, preferably meeting said Biocompatibility specifications, is selected from steel, ceramic and/or plastic, more preferably selected from a class of terpolymers, even more preferably selected from acrylonitrile-butadiene-styrene-copolymers. Also preferred is the selection of device material from any acrylonitrile butadiene styrene, such as Lustrian® 633 ABS (natural) (Bayer). Even more preferably is that the device according to the present invention is sterilizable and biocompatible and thus especially suitable for medical use. Preferably, the puncture device guide according to the present invention is assembled of multiple parts or components, preferably 1 to 10 parts or components, more preferably 1 to 6, even more preferably 5 or 6 parts or components. Preferably the puncture device guide according to the present invention is assembled of 5 different parts or components, preferably of the adapter 105, the body member 110, the slide member 115, the cradle member 120 and the cartridge member 125. If the puncture device guide according to the present invention comprises a guide plate 130, 1130, it is preferably assembled of 6 different parts or components, namely, preferably of the adapter 105, the body member 110, the slide member 115, the cradle member 120, the cartridge member 125 and the guide plate 130, 1130. These components are preferably each made from a single molding. Preferably the number of molds required for production of puncture device guide parts or components is equal to- or less than the number of parts or components. Preferably the number of molds required for production of puncture device parts or components is 1 to 10, more preferably is 1 to 6, even more preferably is 5 or 6. Preferably 5 or 6 different molds are required for production of the component of the puncture device guide. More preferably each of the 5 or 6 molds is designed to produce each one of the parts or components of the puncture device guide comprising an adapter 105, body member 110, slide member 115, cradle member 120, cartridge member 125 and optionally guide plate 130, 1130. Also preferred is that one or more of the different components or parts is produced multiple times for use with one patient wherein preferably one or more parts will be interchanged when multiple injections are performed in one patient. Preferably, the guide plate 130, 1130 is produced multiple times so that a new guide plate 130, 1130 can be used after each injection. Preferably, the puncture device guide according to the present invention has a length of about 5 to about 30 cm, a width of about 1 cm to about 5 cm and a height of about 1 cm to about 5 cm in order to be suitable for medical use. Thus, in a preferred embodiment of the present invention the puncture device guide is (a) sterilizable, preferably by treatment with ethylene oxide, moist heat, dry heat, radiation, vaporized hydrogen peroxide, chlorine gas, vaporized peracetic acid and/or nitrogen dioxide, and/or (b) biocompatible, preferably due to selection of a material selected from steel, ceramic, and/or plastic. Even more preferably the device is made of sterilizable plastic, more preferably a terpolymer, even more preferably acrylnitril-butadien-stryol-copolymer.

The present invention also provides a puncture device guide as described herein for use in a method for treatment of the human or animal body by surgery or therapy. In particular, the present invention provides a puncture device guide as described herein for use in a method of treating and/or preventing urinary incontinence, anal incontinence, overactive bladder, underactive bladder, anal fistula(s), hemorrhoids, (chronic) inflammation, myopathies, neuropathies, and/or prostate malignancies. Preferably in such methods, pharmaceutically active substances and/or compositions are administered into the site of injury or disease. Preferably in such methods for treating and/or preventing urinary- and/or anal incontinence, pharmaceutically active substances and/or compositions are administered into the anal- and/or urinary sphincter apparatus. Preferably in such methods for treating and/or preventing overactive and/or underactive bladder, the pharmaceutically active substances and/or compositions are administered into the bladder. Preferably in such methods for treating and/or preventing anal fistula(s), the pharmaceutically active substances and/or compositions are administered into the anal fistula(s). Preferably in such methods for treating and/or preventing hemorrhoids, the pharmaceutically active substances and/or compositions are administered into the hemorrhoids. Preferably in such methods for treating and/or preventing prostate malignancies, the pharmaceutically active substances and/or compositions are administered into the malignant prostate tissue. Preferably in such methods for treating and/or preventing chronic inflammation, myopathies or neuropathies, the pharmaceutically active substances and/or compositions are administered into the site of inflammation, site of manifested myopathy, or site of manifested neuropathy, respectively. Preferably pharmaceutically active substances are selected from autologous and/or allogenic cells. In one embodiment of the present invention, the puncture device guide is used for injection procedures of cells as already disclosed in EP2120976B1. Administering cells into a given tissue or site of injury comprises a therapeutically effective number of cells in solution or suspension, e.g., about $1 \times 10^6$ to about $6 \times 10^6$ cells per 100 µl of injection solution. The injection solution is preferably a physiologically acceptable medium, with or without autologous serum. Physiological acceptable medium can be by way of nonlimiting example physiological saline, or a phosphate buffered solution. Preferably, cells are administered into the anal sphincter apparatus as a treatment for anal incontinence to enhance, improve, and/or repair the external and/or internal anal sphincter. Preferably, the cells are injected into or adjacent to the external and/or internal anal sphincter and survive and differentiate into mature muscle cells to augment the sphincter and/or improve sphincter function. The feasibility and long-term survival of myogenic progenitor cells in accordance with this embodiment has been shown before (Messner et al., 2021; Thurner et al., 2020). Alternatively preferred is that the puncture device guide is used for prevention of anal incontinence by administering cells into thereby augmenting and/or strengthening the existing incontinence apparatus. Feasibility of cells administration into muscle tissue for treatment of fecal incontinence has been already demonstrated (Frudinger et al., 2018). The inventors found that the puncture device guide according to the present invention is especially useful for prevention and/or treatment of anal incontinence as it is especially accurate and safe for injecting a needle into the anal sphincter apparatus and/or administering cells into the anal sphincter apparatus. The increased accuracy as well as safety of the device according to the present invention might lead to more effective prevention and/or treatment of diseases.

The present invention also provides a guide plate (130, 1130) as described herein. Said guide plate comprises preferably a hole (606) to receive the needle (25) therethrough, a boss (608, 1108) configured to be received by the tip guide (135, 1135) of a puncture device guide according to the present invention. The guide plate (130, 1130) further comprises preferably a coupling element (602) configured to removably attach the guide plate (130, 1130) to the tip guide (135, 1135) of a puncture device guide according to the present invention. Preferably, the guide plate (130, 1130) further comprises: multiple holes (606) at different radial distances, wherein each of the multiple holes (606) corresponds to one of the radial distances for the path of the needle (25) of a puncture device guide according to the present invention. The guide plate (130, 1130) may further comprise a release hole (604) adjacent the coupling element (602), wherein the release hole (604) is configured to receive a tab (360) therein that releases the coupling element (602) from the tip guide (135, 1135) of a puncture device guide according to the present invention.

Although the invention has been described in detail above, it is expressly understood that it will be apparent to persons skilled in the relevant art that the invention may be modified without without departing from the spirit of the invention. Various changes of form, design, or arrangement may be made to the invention without departing from the scope of the invention. Different combinations illustrated above may be combined in a single embodiment. Therefore, the above-mentioned description is to be considered exemplary, rather than limiting, and the true scope of the invention is that defined in the following claims.

The following examples explain the present invention but are not considered to be limiting.

Example 1—Force Measurements by Needle Deflection

Figure 14:
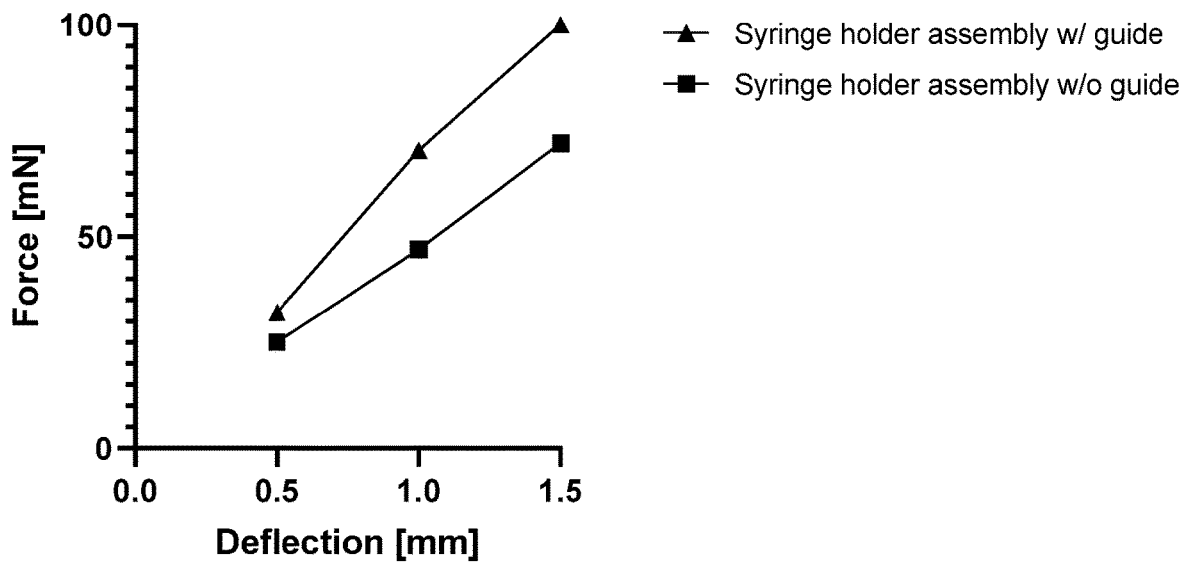
FIG. 14 demonstrates the results of force measurements when deflecting needles are attached to a syringe holder assembly with a guide (w/) or without a guide (w/o).

Syringe holder assemblies according to FIG. 7 were tested when guide plate (130) was attached or not to demonstrate the functional effect of such guide plate. Terumo Agani 21Gx2" (0.8*50 mm) Regular Bevel 110 needle (Ref. AN*2150R1) was used as puncture device (25) in the assembly and was attached to a 1 mL B-Braun Injekt®-F Tuberkulin syringe (REF: 9166017V) (130). Syringe and needle were attached to the syringe holder of FIG. 7 either using guide plate (130) or not and then attached to a BK8848 ultrasound probe. Next, a force transducer (F30 HSE Force Transducer Type 372 Serial no.: 97551) was attached to a Venier control Type 805 (Hugo Sachs Elektronik, HSE, Germany. Range: 0-20 mm, resolution 0.5 mm/turn) for uniaxial movement. The force transducer was calibrated using a 10 mN calibration weight (HSE calibration weight 1 cN=10 mN=1 Gramm) by an amplifier (TAM-A Transducer Amplifier Module Plugsys from HSE) attached to a personal computer running ACAD Data acquisition software (HSE, Germany) for windows to receive and demonstrate the measured forces. Afterwards, the syringe holder assemblies (with or without guide plate) were slide along the axis of the probe adapter (105) to reach the configuration like FIG. 8A. Next, the tip of the needle was placed on the hook of the force transducer, the ultrasound probe fixed and the vernier control turned to result in axial movement of the needle in steps of 0.5 mm from 0.5 mm to 1.5 mm. At every step, generated force on the force transducer was recorded as a measure of how stable the needle is fitted within the assembly. Higher forces were interpreted as higher stability, as more force is required to deflect the needle. Results of the measurements are demonstrated in Table 1 and FIG. 14. It was found that higher forces in syringe holder assembly with guide plate compared to syringe holder assembly without guide plate were recorded at 0.5 mm, 1.0 mm, and 1.5 mm deflection of the needle tip. No difference could be determined at 2.0 mm deflection due to the maximum detectable force of the system.

TABLE 1

Results of force measurements on needle tips at different deflections when attached to different syringe holder assemblies.

| Deflection [mm] | Force generated [mN] | |
|---|---|---|
| | Syringe holder assembly (Without guide plate) | Syringe holder assembly (With guide plate) |
| 0.5 | 25.0 | 32.1 |
| 1.0 | 47.0 | 70.4 |
| 1.5 | 72.0 | ≥100 |
| 2.0 | ≥100 | ≥100 |

Example 2—Guidance Accuracy Measurements in Muscle Tissue

In order to address the accuracy of guiding a puncture device through muscular tissue, different syringe holder assemblies (one equivalent to EP2170440A2 and a device according to FIG. 7 either including or excluding guide plate 130) were attached to a BK8848 ultrasound transducer, which was covered with a transducer gel filled latex cover. Each syringe holder assembly was then equipped with BBraun 1 ml syringes as well as 21 gauge long lancet regular bevel needles. The BK8848 ultrasound transducer was attached to a BK FlexFocus Ultrasound System for visualization of signals recorded by the transducer. Syringe holder assemblies were placed into a water bath and the needle was guided forward along the axis of the BK8848 force transducer until the tip of the needle was reaching the transversal detection window of the transducer. The needle tip visible in the ultrasound system for each syringe holder assembly was marked with an "x" to allow for later measurement of accuracy when guiding a puncture device in a tissue. Porcine muscle tissue was prepared by cutting holes into the tissue using scalpels to allow the BK8848 transducer enter the hole, thereby resembling an endocavity examination. Next, each syringe holder assembly was used to guide a total of 12 needles into individual sites of the muscle tissue each up to a maximum of 5 cm depth which should allow the needle to reach the window of the transducer sensor. For each needle penetrating the muscle tissue, the position of the needle tip visible in the ultrasound system was marked and the distance from the previously set "x" position was measured in mm in order to understand how much the needle was deflected when moving through the muscle tissue. Mean and standard deviation values of repeated measures were calculated in order to compare accuracy of each syringe holder assembly. As it is visible in Table 2, syringe holder assembly of the present invention including guide plate 130 was leading to lowest needle deflection of 1.92±0.58 mm as compared to a device equivalent to EP2170440A2 leading to 1.98±0.35 mm deflection and the syringe holder assembly of FIG. 7 excluding the guide plate 130 leading to 2.23±0.85 mm deflection of the needle.

TABLE 2

Results of needle deflection measurements in porcine muscle tissue.

| Syringe holder assembly | Deflection of needle tip in muscle tissue compared to target location in water bath [mm] |
|---|---|
| According to FIG. 7 with guide plate 130 | 1.92 ± 0.58 |
| According to FIG. 7 without guide plate 130 | 2.23 ± 0.85 |
| According to EP2170440A2 | 1.98 ± 0.35 |

REFERENCES

Frudinger, A., Marksteiner, R., Pfeifer, J., Margreiter, E., Paede, J., Thurner, M., 2018. Skeletal muscle-derived cell implantation for the treatment of sphincter-related faecal incontinence. Stem Cell Research & Therapy 9, 233.

Messner, F., Thurner, M., Müller, J., Blumer, M., Hofmann, J., Marksteiner, R., Couillard-Despres, S., Troppmair, J., Öfner, D., Schneeberger, S., Hautz, T., 2021. Myogenic progenitor cell transplantation for muscle regeneration following hindlimb ischemia and reperfusion. Stem Cell Res Ther 12, 146.

Thurner, M., Deutsch, M., Janke, K., Messner, F., Kreutzer, C., Beyl, S., Couillard-Després, S., Hering, S., Troppmair, J., Marksteiner, R., 2020. Generation of myogenic progenitor cell-derived smooth muscle cells for sphincter regeneration. Stem Cell Res Ther 11, 233.

The invention claimed is:

1. A puncture device guide, comprising:
an adapter (105) configured to fixedly attach to an ultrasound probe (10);
a syringe holder assembly (140) configured to slidingly attach to the adapter (105) and receive a syringe (15) therein;
wherein the syringe holder assembly (140) is configured to slide on probe adapter (105) in an axial direction relative to the ultrasound probe (10);
wherein the syringe holder assembly (140) is configured to allow for selective adjustment of a radial distance for a path of a needle (25) of the syringe (15) relative to the ultrasound probe (10);

wherein the adapter (105) includes a tip guide (135, 1135) to selectively align a distal end of the needle (25) with the radial distance for the path;

wherein, when the ultrasound probe (10) is inserted into a patient, the syringe assembly is configured to slide forward on the adapter to insert the needle past the tip guide into a patient; and wherein the puncture device guide further comprises:
    a guide plate (130, 1130), the guide plate including:
        a hole (606) to receive the needle (25) therethrough,
        a boss (608, 1108) configured to be received by the tip guide (135, 1135), and
        a coupling element (602) configured to removeably attach the guide plate (130, 1130) to the tip guide (135, 1135), and wherein:
    the tip guide (135, 1135) further comprises:
        multiple slots (1107) at different radial distances configured to receive the boss (608, 1108) of the guide plate (130, 1130), and
            wherein each of the multiple slots (1107) corresponds to one of the radial distances for the path of the needle (25).

2. The puncture device of claim 1, wherein the guide plate (130, 1130) further comprises:
multiple holes (606) at different radial distances, wherein each of the multiple holes (606) corresponds to one of the radial distances for the path of the needle (25).

3. The puncture device guide according to claim 1, wherein the guide plate (130, 1130) further comprises:
a release hole (604) adjacent the coupling element (602), wherein the release hole (604) is configured to receive a tab (360) therein that releases the coupling element (602) from the tip guide (135, 1135).

4. The puncture device guide of claim 3, wherein the syringe holder assembly (140) further comprises the tab (360), and
wherein, the syringe holder assembly (140) slides forwards on the adapter (105), the tab is inserted into the release hole (604) to release the coupling element (602) and attach the guide plate (130) to the syringe holder assembly (140).

5. The puncture device guide according to claim 1, wherein the syringe holder assembly (140) is configured to slide backwards on the adapter (105) to retract the needle (25) from the patient and back past the tip guide (135, 1135), and
wherein, when the syringe assembly (140) slides backwards, the guide plate (130, 1130) stays attached to the tabs.

6. The puncture device guide according to claim 1, wherein the syringe assembly (140) is configured to slide backwards on the adapter (105) to retract the needle (25) from the patient and back past the tip guide (135, 1135).

7. A method of performing an injection, the method comprising:
attaching a probe adapter (140) to an ultrasound probe (10), wherein the probe adapter (105) includes a tip guide (135, 1135) at a distal end;
attaching a syringe holder assembly (140) to the probe adapter (140), wherein the syringe holder assembly is longitudinally slidable relative to the probe adapter (140);
inserting the ultrasound probe (10) into a patient;
adjusting the syringe holder assembly (140) to provide a selected radial distance for a syringe needle (25) from the ultrasound probe (10);
inserting the syringe (15) into the syringe holder assembly (140) and aligning a syringe needle (25) with the tip guide (135, 1135);
sliding the syringe holder assembly (140) distally to push the needle past the tip guide (135, 1135) and into the patient;
sliding the syringe holder assembly (140) back to retract the needle (25) from the patient, and
removing the syringe (15) from the syringe holder assembly (140), wherein:
the puncture device guide further comprises:
    a guide plate (130, 1130), the guide plate including:
        a hole (606) to receive the syringe needle (25) therethrough,
        a boss (608, 1108) configured to be received by the tip guide (135, 1135), and
        a coupling element (602) configured to removeably attach the guide plate (130, 1130) to the tip guide (135, 1135), and wherein:
    the tip guide (135, 1135) further comprises:
        multiple slots (1107) at different radial distances configured to receive the boss (608, 1108) of the guide plate (130, 1130), and
            wherein each of the multiple slots (1107) corresponds to one of the radial distances for the path of the syringe needle (25).

8. The method of claim 7, wherein inserting the syringe (15) into the syringe holder assembly (140) further comprises:
providing a guide plate (130, 1130) with a boss (608, 1108) configured to be received by the tip guide (135, 1135) and a coupling element (602) configured to removably attach the guide plate (130, 1130) to the tip guide (135, 1135);
inserting the syringe needle (25) through a hole (606) in the guide plate (130, 1130), and
inserting the syringe (15) into the syringe holder assembly (140) after inserting the syringe needle (25) through the hole (606).

9. The method according to claim 7, wherein inserting the syringe (15) into the syringe holder assembly (140) further comprises:
selecting the hole from multiple holes (1107) in the tip guide (1135), wherein each of the multiple holes (1107) correspond to a different radial distance for the syringe needle (25) from the ultrasound probe (10).

10. The method according to claim 7, wherein inserting the syringe (15) into the syringe holder assembly (140) further comprises:
sliding the guide plate (130, 1130) along the syringe needle (25) until the guide plate (130, 1130) attaches to the tip guide (135, 1135).

11. The method according to claim 7, wherein sliding the guide plate (130, 1130) along the syringe needle (25) until the guide plate (130, 1130) attaches to the tip guide (135, 1135) further comprises:
moving the guide plate (130, 1130) to engage the boss (608, 1108) with one of multiple slots on the tip guide (135, 1135), wherein each of the multiple slots correspond to a different radial distance for the syringe needle (25) from the ultrasound probe (10).

12. The method according to claim 7, wherein, when sliding the syringe holder assembly (140) back to retract the needle (25) from the patient, the syringe needle (25) does not contact the tip guide (135, 1135).

13. The method according to claim 7, wherein, sliding the syringe holder assembly (140) distally to push the needle

(25) past the tip guide (135, 1135) and into the patient, the syringe holder assembly (140) engages the guide plate (130, 1130) and release the guide plate (130, 1130) from attachment to the tip guide (135, 1135).

14. The method according to claim 7, wherein, when sliding the syringe holder assembly (140) back to retract the needle (25) from the patient, the syringe holder assembly (140) retracts the guide plate (130, 1130) away from the tip guide (135, 1135).

15. The method according to claim 7, further comprising:
   detaching the guide plate (130, 1130) from the syringe holder assembly (135, 1135) by sliding the guide plate (130, 1130) distally along a portion of the syringe needle (25).

16. The method according to claim 7, wherein removing the syringe (15) from the syringe holder assembly (140) further comprises:
   removing the syringe (15) and the guide plate (130, 1130) while the syringe needle (25) remains inserted through the guide plate (130, 1130).

17. The method according to claim 7, wherein the method further comprises that the syringe (15) to be inserted into the syringe holder assembly (140) for aligning a syringe needle (25) with the tip guide (135, 1135) is filled with a substance or composition and wherein sliding the syringe cartridge (125) inserted with a syringe (15), filled with a substance or composition, back, results in simultaneously administering the substance or composition into the patient.

18. The puncture device guide according to claim 1 configured for medical use, in particular configured to perform a method according to claim 7.

19. A puncture device guide according to claim 1, wherein the device is at least one of
   (a) sterilizable by treatment with at least one of ethylene oxide, moist heat, dry heat, radiation, vaporized hydrogen peroxide, chlorine gas, vaporized peracetic acid and nitrogen dioxide, and
   (b) biocompatible due to selection of at least one of a material which is selected from steel, ceramic, plastic, a terpolymer, and a acrylnitril-butadien-styrol-copolymer.

* * * * *